（12）United States Patent
Hinds, III

(10) Patent No.: US 7,611,628 B1
(45) Date of Patent: Nov. 3, 2009

(54) ALIGNED NANOTUBULE MEMBRANES

(75) Inventor: Bruce J. Hinds, III, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 832 days.

(21) Appl. No.: 11/128,443

(22) Filed: May 13, 2005

Related U.S. Application Data

(60) Provisional application No. 60/570,927, filed on May 13, 2004.

(51) Int. Cl.
B01D 71/06 (2006.01)
B01D 39/10 (2006.01)
B01F 9/12 (2006.01)

(52) U.S. Cl. .............. 210/500.27; 210/490; 423/447.1; 977/888; 977/742; 977/745; 977/746; 977/778; 264/45.1

(58) Field of Classification Search ................ 210/500.27–500.43, 490; 423/447.1; 977/742–746, 977/778, 763, 877, 888, 963; 264/45.1
See application file for complete search history.

(56) References Cited

U.S. PATENT DOCUMENTS

| 6,203,814 | B1 | 3/2001 | Fisher et al. | |
|---|---|---|---|---|
| 6,426,134 | B1 | 7/2002 | Lavin et al. | |
| 7,056,455 | B2 | 6/2006 | Matyjaszewski et al. | |
| 7,115,306 | B2 * | 10/2006 | Jeong et al. | 427/577 |
| 7,229,556 | B1 * | 6/2007 | Hinds et al. | 210/652 |
| 7,290,667 | B1 * | 11/2007 | Bakajin et al. | 210/503 |
| 7,459,121 | B2 * | 12/2008 | Liang et al. | 264/555 |
| 7,510,695 | B2 * | 3/2009 | Smalley et al. | 423/447.3 |
| 2003/0077515 | A1 | 4/2003 | Chen et al. | |
| 2003/0111333 | A1 | 6/2003 | Montgomery et al. | |
| 2003/0116503 | A1 | 6/2003 | Wang et al. | |
| 2003/0124717 | A1 | 7/2003 | Awano et al. | |
| 2003/0143453 | A1 | 7/2003 | Ren et al. | |
| 2003/0165648 | A1 | 9/2003 | Lobovsky et al. | |
| 2004/0007528 | A1 | 1/2004 | Bakajin et al. | |
| 2004/0038251 | A1 | 2/2004 | Smalley et al. | |
| 2004/0058153 | A1 | 3/2004 | Ren et al. | |
| 2004/0071949 | A1 | 4/2004 | Glatkowski et al. | |

OTHER PUBLICATIONS

G. Che et al. Chemical Vapor Deposition Based Synthesis of Carbon Nanotubes and Nanofibers Using a Template Method. Chem. Mater, vol. 10, 1998, pp. 260-267.

(Continued)

Primary Examiner—Ana M Fortuna
(74) Attorney, Agent, or Firm—King & Schickli, PLLC

(57) ABSTRACT

A method is provided for producing a permeable membrane, comprising the steps of aligning a plurality of hollow nanotubules to form a mat, coating the mat with a continuous polymer matrix to form a membrane. The membrane is etched (a) to open the plurality of hollow nanotubules and form pores and (b) to oxidize the carboxyl groups to carboxylate groups. At least one additional functional unit having at least one available amine group to bind the at least one additional functional unit to the nanotubule end carboxylate group may be provided. Membranes fabricated in accordance with the method of the invention are provided also.

90 Claims, 9 Drawing Sheets

OTHER PUBLICATIONS

Li Sun et al. Single Carbon Nanotube Membranes: A Well-Defined Model for Studying Mass TRansport through Nanoporous Materials. J. Am. Chem. Soc. 2000, vol. 122, pp. 12340-12345.

M.J. Casavant et al. Neat Macroscopic Membranes of Aligned Carbon Nanotubes. Journal of Applied Physics, vol. 93, No. 4, Feb. 15, 2003 pp. 2153-2156.

A. Srivasta et al. Carbon Nanotube Filters. Nature Materials, vol. 3., Sep. 2004, pp. 610-614; published on line 1 Aug. 2004.

Nachiket R. Raravikar et al. Synthesis and Characterization of Thickness-Aligned Carbon Nanotube-Polymer Composite Films. Chem. Mater. 17 (5), 974-983, 2005.

* cited by examiner

Fig. 1
Fig. 2
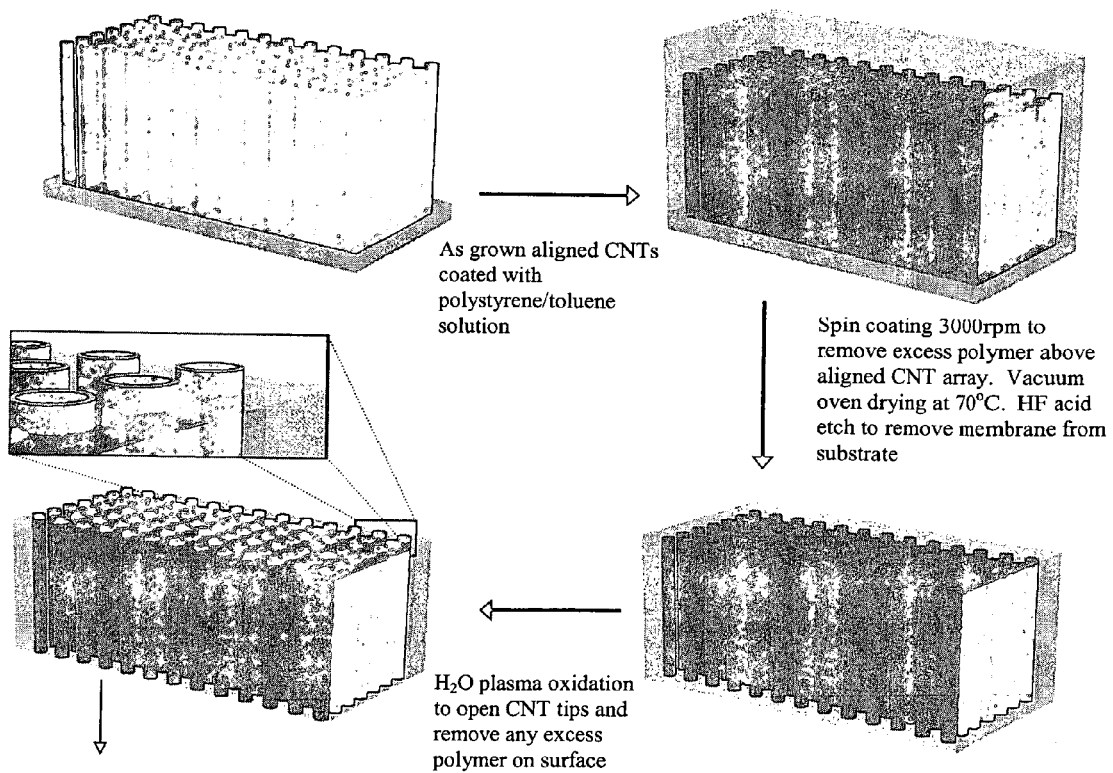

c —— 2-Aminoethanethiol functionalized CNTs
b —— Plasma oxidized CNTs
a ------ CNTs after CVD growth

ALIGNED NANOTUBULE MEMBRANES

This application claims the benefit of U.S. Provisional Patent Application Ser. No. 60/570,927, filed May 13, 2004.

TECHNICAL FIELD

The present invention relates to nanoporous membranes. Specifically, the invention relates to methods for fabricating nanoporous membranes comprising aligned nanotubules, and to membranes fabricated thereby. The membranes of the present invention can be functionalized for selective transport of various target molecules therethrough.

BACKGROUND OF THE INVENTION

Advances in nanoporous membrane design with improvements in chemical selectivity and high flux may directly benefit a number of fields, including chemical separations, ion channel mimetics, drug delivery, and wastewater remediation. Matching pore size of such membranes to target molecule size is important in that it allows molecular sieving and forces interactions with chemically selective molecules associated with the membrane pore. This is a particularly difficult challenge in the nanometer pore size range.

Various approaches have been investigated, including inorganic materials such as inorganic porous ceramic membranes, silica, alumina, zirconia, zeolite, and carbon. Inorganic membranes are very robust, and do not suffer from solvent effects. However, high surface area inorganic membranes are expensive and mechanically fragile. Organic membranes are most prevalent, but suffer from difficulty in regulating pore size, and also from solvent effects (swelling) which alter pore size, affecting selectivity and throughput. Exemplary organic membranes studied include functionalized polymer affinity membranes, block copolymers, and mesoporous macromolecular architectures.

Nanometer-scale control of pore geometry and demonstration of molecular separations have been achieved also through the plating of nanoporous polycarbonate ion track-etch and ordered alumina membranes with initial pore dimensions of approximately 20 to 50 nm. A major challenge to improving selectivities of pore-plated membranes is minimizing the variations in initial alumina pore diameters, because the resultant diameter is the difference between the plating thickness and the initial pore diameter. It is accordingly desirable to begin with a membrane structure having an initial pore diameter near that of the target molecule(s), with limited dispersion.

It is also desirable for such nanoporous membranes to be reversibly gated, to mimic natural biological systems such as for example the nicotinic acetylcholine receptor, which is one of the most widely studied ligand-gated ion channels. In this field, organic membranes such as aromatic/polycarbonate copolymers, cellulose acetate, aliphatic polyamides, polyimides, polydimethylsiloxone, and polysulfone have been studied. In particular, polysulfone membranes have been evaluated for use as affinity membranes. Hydrogels have also been studied for use as gated membranes due to their reversible phase change, which is mostly controlled by external chemical stimuli such as pH, temperature, or variation in electric charge. However, molecular diffusivity is low in hydrogels because of restricted chain mobility. Further, volume changes in hydrogel require a lag time, and hydrogel membranes lack mechanical stability.

The present invention addresses the identified need in the art by providing a method for fabricating a nanoporous ordered membrane, and a membrane fabricated thereby. Advantageously, the membrane of the present invention is stable and provides a tightly controlled pore size, and is resistant to solvent effects. Still further, the membrane of the present invention can be functionalized in a variety of ways at the pore openings to impart selectivity to the membrane, to provide a selectively gateable membrane as well as other functions.

SUMMARY OF THE INVENTION

In accordance with the purposes of the present invention as described herein, a method is provided for producing a permeable membrane, comprising the steps of aligning a plurality of hollow nanotubules to form a mat, coating the mat with a continuous polymer matrix to form a membrane, and etching the membrane (a) to open the plurality of hollow nanotubules and form pores and (b) to oxidize an end of the nanotubules to form carboxylate groups. Each of the plurality of nanotubules typically includes a hydrophobic lumen. The nanotubules may be selected from the group consisting of multi-walled carbon nanotubes, single-walled carbon nanotubes, self-assembling macromolecular tubules comprising peptides and porphyrins, or any combination thereof. The polymer matrix may be a thermoset resin, a soluble cast polymer, or a castable solidifying sol-gel solution. Typically, the polymer matrix is selected from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

In one embodiment, the aligned nanotubule mat is coated by dissolving the polymer matrix in a suitable solvent, followed by spin-coating the mat with the polymer-solvent mix. The mat may also be coated by high-velocity rinsing of the mat with the polymer-solvent mix, to remove excess polymer from the top surface. The aligned hollow nanotubules may be assembled in situ on a substrate, followed by removing the substrate after coating with the polymer matrix. The etching step is typically performed using an oxidative method. The etching method may be selected from the group consisting of plasma oxidation, electrochemical oxidation, anodic oxidation, exposure to an oxidizing acid, exposure to ozone, exposure to peroxide, exposure to permanganate, or combinations thereof. In one embodiment, the membrane is selectively etched whereby the plurality of nanotubules are shortened to a length that is less than a dimension of the polymer matrix.

The method of the present invention further contemplates the step of binding at least one additional functional unit to the carboxylate groups. It will be appreciated that for purposes of the present disclosure, the term "additional functional unit" is understood to mean individual atoms or ions, individual molecules, or molecular complexes comprising two or more interacting molecules, having the properties described more fully infra. The at least one additional functional unit typically includes at least one available amine group to bind to the nanotubule end carboxylate group. In one embodiment, the at least one additional functional unit is adapted to selectively open or at least partially occlude the pore of an adjacent nanotubule. In another embodiment, the at least one additional functional unit changes conformation to selectively expose or to at least partially occlude the pore of the adjacent nanotubule in response to an application of an electrical impulse to the membrane.

The functional unit may be selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof. In particular embodiments of the invention, the at least one additional functional unit is selected from the group consisting of biotin, avidin, streptavidin, aliphatic amines, charged dyes, anionic or cationically charged ligands, catalytic metals, catalytic coordination compounds, and any combination thereof.

In another aspect, the present invention provides an ordered nanoporous permeable membrane, comprising a plurality of aligned hollow nanotubules and coated with a continuous polymer matrix to form a membrane, wherein the membrane is etched (a) to open the plurality of hollow nanotubules and form pores and (b) to oxidize an end of the nanotubules to form carboxylate groups. Each of the plurality of nanotubules may include a hydrophobic lumen. The nanotubules may be selected from the group consisting of multi-walled carbon nanotubes, single-walled carbon nanotubes, self-assembling macromolecular tubules comprising peptides and porphyrins, and any mixture thereof. The polymer matrix may be a thermoset resin, a soluble cast polymer, or a castable solidifying sol-gel solution, and may be selected from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

As discussed above, the aligned hollow nanotubules may be assembled in situ on a substrate, coated with the polymer matrix, and removed from the substrate after coating. The polymer matrix may be etched using an oxidative method selected from the group consisting of plasma oxidation, electrochemical oxidation, anodic oxidation, exposure to an oxidizing acid, exposure to ozone, exposure to peroxide, exposure to permanganate, and any combination thereof, and in one embodiment is etched selectively whereby the plurality of nanotubules are shortened to a length that is less than a dimension of the polymer matrix. In this latter embodiment, the membrane is selectively etched by electrochemical oxidation.

The membrane fabricated in accordance with the present invention may further include at least one additional functional unit bound to the carboxylate groups. Typically, the at least one additional functional unit includes at least one available amine group to bind the at least one additional functional unit to the nanotubule end carboxylate group. In one embodiment, the at least one additional functional unit is adapted to selectively open or to at least partially occlude the pore of an adjacent nanotubule. In another embodiment, the at least one additional functional unit changes conformation to selectively expose or to at least partially occlude the pore of the adjacent nanotubule in response to an application of an electrical impulse to the membrane, such as for example Direct Blue Dye 71. The at least one additional functional unit may be selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof. In particular embodiments, the at least one additional functional unit is selected from the group consisting of biotin, avidin, streptavidin, aliphatic amines, charged dyes, anionic or cationically charged ligands, catalytic coordination compounds, catalytic metals, and any combination thereof.

In yet another aspect of the present invention, a method for altering flux of a target molecule through an ordered nanoporous permeable membrane is provided. The method of producing the membrane is substantially as described above, comprising aligning a plurality of hollow nanotubules having a carboxyl group near an end thereof to form a mat, coating the mat with a continuous polymer matrix to form a membrane, etching the membrane (a) to open the plurality of hollow nanotubules and form pores and (b) to oxidize an end of the nanotubules to form carboxylate groups, and binding at least one additional functional unit to the carboxylate groups to alter a flux rate of a predetermined target molecule through the permeable membrane. The at least one additional functional unit includes at least one available amine group to bind the at least one additional functional unit to the nanotubule end carboxylate group, and is substantially as described above.

The at least one additional functional unit is selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof. Typically, a functional unit will be selected which reversibly binds the target molecule. The method of this invention further includes the step of adding a displacing molecule which displaces the reversibly bound target molecule from the at least one additional functional unit.

In one embodiment of this method, flux of a target molecule is altered by at least partially occluding the pore of the adjacent nanotubule to a predetermined degree. In one embodiment, the step of at least partially occluding the pore of the adjacent nanotubule may be achieved by selecting the at least one additional functional unit having a length suitable to occlude the pore of the adjacent nanotubule to the predetermined degree. In another embodiment, the step of occluding the pore of the adjacent nanotubule to the predetermined degree is achieved by adding a predetermined number of spacer molecules to the at least one additional functional unit to alter a length thereof. In yet another embodiment, flux of a target molecule is altered by selecting as the at least one additional functional unit a molecule which changes conformation to expose or to at least partially occlude the pore of the adjacent nanotubule in response to an application of an electrical impulse to the membrane.

In still yet another aspect of the present invention, a method is provided for increasing flux of a target molecule through an ordered, nanoporous permeable membrane, comprising aligning a plurality of hollow nanotubules having a carboxyl group near an end thereof to form a mat, coating the mat with a continuous polymer matrix to form a membrane, and selectively etching the membrane (a) to open the plurality of hollow nanotubules and form pores and (b) to oxidize an end of the nanotubules to form carboxylate groups. The step of selectively etching the membrane is performed whereby the plurality of nanotubules are shortened to a length that is less than a dimension of the polymer matrix, providing a path for flux of the target molecule that is less than the dimension of the polymer matrix. The nanotubules, polymer matrix, and coating step are substantially as described above. Typically, the step of selectively etching the membrane is performed by electrochemical oxidation. Additional functional units may be bound to the carboxylate groups, substantially as previously described. In one embodiment, the exposed nanotubule end may be selectively functionalized electrochemically by reduction of functional diazonium salt, with the nanotubule sidewalls remaining protected by the polymer matrix.

In still yet another aspect of the invention, a method is provided for differentially functionalizing opposed sides of an ordered nanoporous permeable membrane fabricated substantially as described above, comprising aligning a plurality of hollow nanotubules having a carboxyl group near an end thereof to form a mat, coating the mat with a continuous polymer matrix to form a membrane, and etching the membrane (a) to open the plurality of hollow nanotubules and form pores and (b) to oxidize an end of the nanotubules to form carboxylate groups. Next, at least one first functional unit is bound to the carboxylate groups on a first side of the membrane, and at least one second functional unit is bound to the carboxylate groups on a second, opposed side of the membrane. The at least one first functional unit may be the same as or different from the at least one second functional unit.

The first and second at least one functional units may be bound to opposed sides of the membrane by the steps of contacting the first side of the membrane with a solution containing the at least one first functional unit, and contacting the second, opposed side of the membrane with a solution containing the at least one second functional unit. The nanotubules, polymer matrix, and method of coating the nanotubules with the polymer matrix are substantially as previously described. The first and second at least one additional functional units include at least one available amine group to bind to the nanotubule end carboxylate group. Molecules suitable for the first and second at least one functional unit are substantially as described above.

In still yet another aspect of the present invention, a differentially functionalized ordered nanoporous permeable membrane, fabricated in accordance with the method described supra, is provided. As noted above, the nanotubules may include a hydrophobic lumen, and may be selected from the group consisting of multi-walled carbon nanotubes, single-walled carbon nanotubes, self-assembling macromolecular tubules comprising peptides and porphyrins, and any mixture thereof. The polymer matrix is substantially as described above. The membrane first and second functional units may be the same, or the first and second functional units may be different.

As should be appreciated, the embodiments shown and described are an illustration of one of the modes best suited to carry out the invention. It will be realized that the invention is capable of other different embodiments and its several details are capable of modification in various, obvious aspects all without departing from the invention. Accordingly, the drawings and descriptions will be regarded as illustrative in nature, and not as restrictive.

BRIEF DESCRIPTION OF THE DRAWINGS

The accompanying drawings incorporated in and forming a part of the specification, illustrate several aspects of the present invention and together with the description serve to explain the principles of the invention. In the drawings:

FIG. 1 is a TEM micrograph showing the cleaved edge of a CNT-polystyrene membrane after exposure to $H_2O$ plasma oxidation, with the polymer matrix slightly removed to contrast the alignment of the CNTs across the membrane (scale bar=2.5 μm);

FIG. 2 schematically depicts the processing scheme for a CNT membrane;

Figure 3:
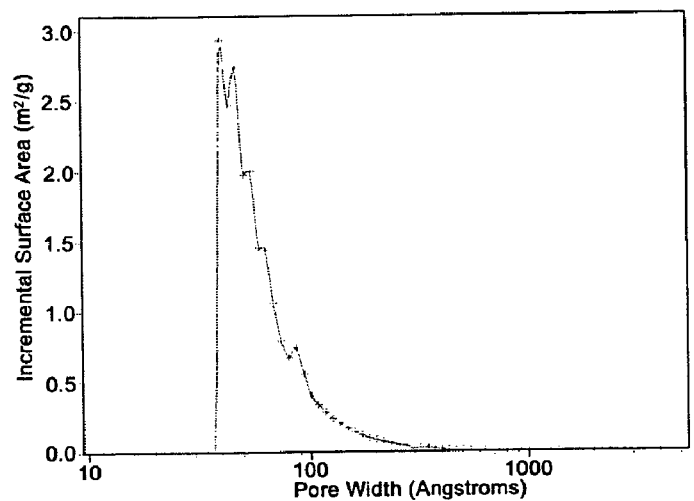
FIG. 3 shows $N_2$ porosity data at 77K for a CNT membrane in accordance with the present invention, showing a pore distribution of 6±2 nm.

Reference will now be made in detail to the present preferred embodiment of the invention, an example of which is illustrated in the accompanying drawings.

DETAILED DESCRIPTION OF THE INVENTION

The following examples are presented in support of and to further illustrate the invention as described above, but are not to be considered as limited thereto.

Example 1

An aligned carbon nanotube (CNT) membrane was prepared. Aligned CNT's were grown in situ using substantially the methods described in R. Andrews et al., *Chem. Phys. Lett.* 303, 467 (1999) (incorporated herein by reference). Briefly, CNT's were grown for 30 min. (with an aligned CNT film thickness of 5 to 10 μm) on quartz substrate, in a chemical vapor deposition process that used a ferrocene-xylene-argon-hydrogen feed at 700° C. A 50 weight-percent solution of polystyrene (PS) and toluene was spin-coated over the surface. PS is known to have high wettability with CNTs, and the CNT array was readily impregnated with PS. Because of the high viscous drag within the CNT array, only excess polymer on top of the composite structure was removed during the spin-coating process. The film was dried in vacuum at 70° C. for 4 days. Hydrofluoric acid was then used to remove the CNT-PS composite from the quartz substrate, to produce a freestanding composite film of 5- to 10 µm thickness. FIG. 1 shows the cleaved edge of the freestanding membrane structure, with CNT alignment intact from top to bottom of the polymer film. A few cut CNTs with high curvature were artifacts of the cleaving and plasma oxidation process. A tortuosity of 1.10 (±0.05) was estimated from the CNT length divided by the film thickness, obtained from cross-sectional micrographs.

We then removed a thin layer of excess polymer from the top surface and opened the CNT tips to form a membrane structure. This was accomplished with $H_2O$ plasma-enhanced oxidation process at 600 mtorr $H_2O$ pressure and 2.4 W/cm$^2$ for 7 min, similar to conditions used to remove Fe nanocrystal catalyst particles from the tips of CNTs.

The overall processing scheme for the CNT membrane is shown in FIG. 2. The plasma oxidation process etched PS faster than CNTs; thus, the CNT tips were 10 to 50 nm above the polymer surface. SEM analysis of this surface gave an estimated areal density of 6 (±3)×10$^{10}$ CNT tips per cm$^2$. Importantly, the plasma process left the tips of the CNTs functionalized with carboxylate groups that could be readily reacted with biomolecules, including a wide variety of selective receptors. Transmission electron microscopy (TEM) of dissolved membranes demonstrated that ~70% of the CNT tips had been opened by the plasma oxidation process under our conditions. Substantial amounts of Fe catalyst were observed in the cores of the CNTs, but were reduced by 24 hours of HCl treatment. Electrical transport measurements were also consistent with the presence of highly conductive CNTs spanning from top to bottom of the insulating polymer film. The conductivity from top to bottom of the membrane (Au film contacts) was 35.2 $\Omega^{-1}$ cm$^{-1}$, whereas a 4-point probe that measured sheet resistance gave an in-plane conductivity value two orders of magnitude less than that at 0.32 2 $\Omega^{-1}$ cm$^{-1}$. Reduced in-plane conductivity was expected, because neighboring CNTs only touched each other with the modest tortuosity seen.

Transport measurements of both gas (N2 and aqueous ionic species [Ru(NH$_3$)$_6$$^{3+}$] were performed to determine transport through the inner cores of the CNTs. For room-temperature $N_2$ permeance measurements, CNT membranes were epoxy-sealed between macroporous, glass-fiber, disk filters and mounted in a gas-flow system equipped with a water manometer. The gas flow volume was measured by a calibrated mass flow meter with the exhaust line at atmospheric ambient pressure. Using Knudsen diffusion, in which the gas-molecule mean free path is limited by pore radius, we calculated the molar flux ($N_a$) as $N_a = \epsilon D_k(P_1-P_2)RTLa$, where $\epsilon$ is the void fraction, $P_1-P_2$ is the pressure difference, R is the universal gas constant, T is the absolute temperature, L is the pore length, a is tortuosity, and $D_k$ is the Knudsen diffusion coefficient, which can be calculated as $D_k=0.97r(T/M_a)^{1/2}$, where r is the mean pore radius and $M_a$ is the molecular weight of the permeate molecule. Using Knudsen diffusion, an observed CNT areal density of 6 (±3)×10$^{10}$ per cm$^2$ mean pore diameter of 7.5 (±2.5) nm, diffusion length of 5 (±1) µm, and tortuosity of 1.10 (±0.05), we calculated a permeance of 2.4 (±1.9) µmol/(m$^2$ s Pa). This is consistent with the observed microstructure of open CNTs that pass across the PS film. A void fraction $\epsilon$ of 0.027 was calculated from the CNT areal density and the inner core cross-sectional area.

FIG. 3 shows pore size distribution from $N_2$ desorption at 77K. The pore size distribution matched that of the CNT inner-core diameter that was observed by TEM and was consistent with the premise of an aligned CNT membrane structure. The porosimeter data on the aligned CNTs without embedded polymer showed a peak of characteristic CNT inner-core diameters (6 to 10 nm) and a very broad tail of 20- to 100-nm pore sizes, which are associated with N2 adsorption on the outer surfaces of CNTs in a densely aligned mesh. When CNTs were embedded within the polymer film, this tail feature did not appear in the porosimeter measurement, which is consistent with a polymer filling the space between the CNTs. Thus, the observed flow through the membrane was through the accessible inner core of the CNTs. The observed pore volume from $N_2$ desorption experiment was 0.073 cm$^3$/g. This is consistent with the estimated pore volume of 0.028 (±0.013) cm$^3$/g calculated from the CNT areal density (6×10$^{10}$ per cm$^2$), the inner core projected area ($\pi r^2$, where 2r=7.5 nm), the tube length (5 µm), the tortuosity (1.10) and the PS density (1.05 g/cm$^3$).

The aligned CNT membrane structure also allowed the transport of Ru(NH$_3$)$_6$$^{3+}$ ions in aqueous solution. A 10-µm-thick membrane was epoxy-sealed to one end of a Pyrex tube, and 400 µL of a 0.01 M Kcl solution was placed inside the Pyrex tube. The membrane was submerged in a 5 mM (Ru (NH$_3$)$_6$Cl$_3$:0.01 M KCl reference solution, to establish a Ru concentration gradient. The inner solution was kept level with the outer reference solution to avoid any pressure-induced transport. The flux of Ru ions passing through the membrane into the inner solution was then determined by cyclic voltammetry.

For the aligned CNT membrane after the $H_2O$ plasma oxidation, a Ru(NH$_3$)$_6$$^{3+}$ flux of 0.07 µmol cm$^{-2}$ hour$^{-1}$ was observed. Treatment of the membrane with HCl for 24 hours aided the ionic flux substantially, increasing it to 0.9 µmol cm$^{-2}$ hour$^{-1}$, presumably by dissolving excess Fe not removed by the plasma process. This flux is comparable to that of ordered alumina membranes showing fluxes of benzonitrile enantiomer of 0.3 µmol cm$^{-2}$ hour$^{-1}$. The diffusion coefficient (D) of Ru(NH$_3$)$_6$$^{3+}$ through the membrane was found to be 2.2 (±0.9)×10$^{-6}$ cm$^{-2}$ s$^{-1}$ from the measured flux, with the areal density, pore diameter, thickness, and tortuosity given previously. This is near the bulk aqueous-solution diffusion of Ru(NH$_3$)$_6$$^{3+}$ of 7×10$^{-6}$ cm$^{-2}$ 5$^{-1}$ (25), indicating only modest interaction of the ion with the CNT tip and the core. We would expect negatively charged carboxylate functional groups at the tips to reduce the observed diffusion coefficient of a positively charged Ru(NH$_3$)$_6$$^{3+}$ ion. In a control experiment, membranes without $H_2O$ plasma treatment did not show ionic transport. Therefore, diffusion through the solid polymer was not significant. Backlit optical microscopy after electrochemical characterization did not show any signs of micro-cracking.

Example 2

Example 1 showed that the open tips of the membrane-bound CNT's were readily functionalizable with carboxylate end groups, which could form the basis for gatekeeper-controlled chemical separations or an ion-channel mimetic sensor. If a selective additional functional unit were placed at the entrance of the CNT and coordinated with a bulky receptor, the CNT pore would be blocked and the ionic flow through the CNT core would be reduced. Ionic flow could be easily detected electrochemically and could provide the basis of a selective sensor system.

Figure 4:
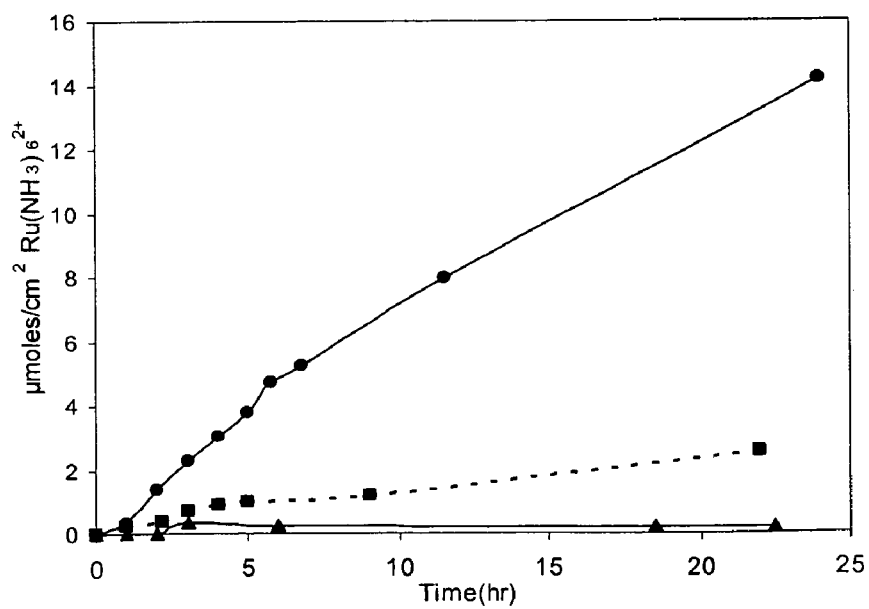
FIG. 4 shows $Ru(NH_3)_6^{3+}$ flux through a CNT membrane structure after HCl treatment (circles), after biotin functionalization (squares), and after streptavidin coordination (triangles)

Accordingly, the well established biotin/streptavidin analyte/receptor system was chosen. A CNT membrane having carboxylate end groups at the CNT pore tips was prepared substantially as described in Example 1. (+)-Biotinyl-3,6 dioxaoctanediamine (Pierce Biotechnology EZ Link) was reacted with the carboxylate end groups of the CNT membrane with a carbodiimide-mediated reaction. This was subsequently coordinated with streptavidin. FIG. 4 shows the flux of $Ru(NH_3)_6^{3+}$ ions for the as-prepared aligned CNT membrane after biotin functionalization and coordination with streptavidin. With the attachment of the biotin tether (2.2 mm long), the $Ru(NH_3)_6^{3+}$ flux was reduced by a factor of 5.5. Simple cross-sectional area reduction of the CNT inner core diameter (from 7.5 mm to 3.1 mm) would reduce ionic flux by a factor of 6.2; thus, this system showed utility for the use of dimensions of attached molecules to further control membrane pore dimensions. The ionic flux was further reduced by a factor of 15 following streptavidin coordination with biotin. This approach of functionalizing the entrance to each CNT pore can be generalized to a variety of biological affinity pairs to block ionic flow through the CNT core when the analyte is present.

Example 3

It was considered that electrochemistry could also be used to tailor the aligned CNT membrane structure. Practical considerations of membrane strength and aligned CNT growth require that the membrane be at least 5 μm thick. However, for large molecular separations based on gate-keeper selectivity, a short path length is desired, because it increases the diffusion flux.

Figure 5A:
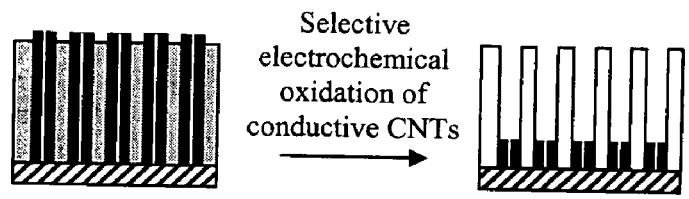
FIG. 5 shows (a) a schematic depiction of selective oxidation of CNTs in a membrane only; and (b) a TEM of the membrane surface after electrochemical oxidation of CNTs at 1.7 V versus Ag—AgCl, below the surface of the contiguous polymer matrix film, with the arrow showing a smaller surface pore nested within a larger surface pore (scale bar=2.5 μm)
Figure 5B:

The CNT length is trimmed by anodically oxidizing the CNT's at ±1.7 V versus an Ag—AgCl reference electrode. Because the PS polymer is an insulator, the conductive CNT's are selectively etched within a polymer matrix. Thus, one can adjust pore length while maintaining the mechanical integrity of the thicker PS matrix. After H2O plasma oxidation, the tips of the CNT's are extending above the surface because the faster etching rate of PS by plasma treatment. FIG. 5a shows a schematic cross section illustration of CNT's selectively oxidized electrochemically inside an insulating PS matrix. FIG. 5b shows the surface after selective electrochemical oxidation. The size of the pores on the PS surface should be at least that of 40-nm outer CNT diameter (FIG. 5a). Because of the tips of the CNT's tend to group together and there is the possibility of localized PS oxidation next to the CNT's, the resulting PS surface pores were often greater than 100 nm. FIG. 5c (arrow) shows an example of a smaller PS surface pore inside a larger PS surface pore, which is consistent with clustering CNT tips at the surface.

Selective reduction of the length of the CNT's within the PS matrix is a valuable tool for tuning membranes to give a required flux while keeping carboxylate functionalization at the tips of CNTs. These carboxylate end groups can then be readily functionalized at the entrance of each CNT inner core to selectively gate molecular transport through the ordered nanoporous membrane for separation and sensing applications.

Example 4

The goal of this study was to switch the functionalized nanopore membranes to on/off state reversibility by attaching and releasing the receptor in a controlled fashion (i.e., receptor-stimulated switching). In the present study, we used a desthiobiotin derivative that binds reversibly to streptavidin to modify the entrance of the through pores of membrane-embedded CNTs, thereby enabling a reversible on/off system. Transport through the nanotube pores was switched off when streptavidin bound to the functionalized membrane, and switched on when streptavidin was released.

DSB-X™ Biotin hydrazide (a desthiobiotin derivative), streptavidin and fluorescein-isothiocyanate labeled streptavidin were purchased from Molecular Probes. Methylviologen (MV2+) and tris(2,2' bipyridyl)dichlororuthenium $(Ru(bpy)_3Cl_2)$ were purchased from Aldrich. 1-ethyl-3-(3-dimethylaminopropyl)carbodiimide (EDC) was purchased from Pierce.

CNT membranes were fabricated using the method substantially as described in Example 1. Briefly, an aligned array of multiwalled CNTs having a mean pore diameter of 7.5± (2.5) nm was grown by chemical vapor deposition using a ferrocene/xylene feed gas. The volume between the CNTs was filled with polystyrene, and the composite film was removed from the quartz substrate with hydrofluoric acid. Excess surface polymer and Fe catalyst nanocrystals at the CNT tips were removed by $H_2O$ plasma oxidation, resulting in a membrane structure with CNT cores traversing the polystyrene film and carboxylate functionalization at the CNT tips.

The CNT membranes were functionalized with DSB-X™ biotin hydrazide, which is a derivative of desthiobiotin that can be attached to carboxylate functionalized CNTs. The conjugation of DSB-X™ biotin hydrazide to the carbon nanotube membrane was carried out in 2-(N-morpholino)ethane sulfonic acid (MES) buffer, pH 6.5. An amount of 20 mg of CNT membrane was added to 4 mL of MES buffer containing 0.015 mg of DSB-X™ biotin hydrazide, and 10 mg of 1-ethyl-3-(3-dimethylaminopropyl)carbodiimide (EDC); the latter was added to activate the carboxylic acid groups present on the membrane. The CNT membrane was incubated in this reaction mixture at 4° C. on a shaker overnight. The CNT membrane was washed thrice with MES buffer to remove any unreacted DSB-X™ biotin hydrazide.

The membranes were characterized by FTIR to confirm the conjugation of DSB-X™ biotin hydrazide. An amount of 2.0 mg of CNT membrane was dried in a vacuum oven, crushed and mixed with 70 mg to KBr to form a pellet. FTIR spectra of the KBr pellet were recorded with a ThermoNicolet Nexus 4700 IR instrument. Next, the DSB-X™ biotin hydrazide functionalized CNT membrane was incubated in a streptavidin solution prepared by dissolving 1.6 mg of streptavidin in 4 mL of Tris buffer (50 mM tris(hydroxymethyl) aminomethane, 50 nN NaCl, pH 8.0). The reaction was carried out at 4° C. overnight on a shaker. The CNT membrane was washed with Tris buffer three times to remove the unreacted streptavidin.

Ionic flux measurements through the CNT membrane were carried out using a simple U-tube cell consisting of two chambers separated by the nanotube membrane. The exposed membrane area was 0.3 cm2. The feed chamber was filled with 7.2 mL of 5 mM aqueous mixture of methylviologen $(MV^{2+})$ and tris(2,2' bipyridyl)dichlororuthenium $(Ru(bpy)_3^{2+})$, and the permeation chamber was filled with 1.4 mL of deionized water. Care was taken to avoid any pressure-induced transport by ensuring that solution levels were at the same height for the two tubes. The permeated solution was periodically assayed using HP 8543 UV-visible spectrophotometer. Calibration plots of each marker molecule ($MV^{2+}$ or $Ru(bpy)_3^{2+}$) in the range $1\times10^{-4}$ M to $1\times10^{-7}$ M (six solutions) were used to quantify the amounts of $MV^{2+}$ and $Ru(bpy)_3^{2+}$ in the permeate solution. The absorbance maximum of $MV^{2+}$ is at 260 nm, and $Ru(bpy)_3^{2+}$ has two peaks at 286 and 452 nm. There is no interference from $MV^{2+}$ at 452 nm, so this wavelength was used to quantify the amount of $Ru(bpy)_3^{2+}$. The $MV^{2+}$ absorbance at 260 nm overlaps with the absorbance from $Ru(bpy)_3^{2+}$. With known $Ru(bpy)_3^{2+}$ concentration (from the 452 nm peak), the overlap can be subtracted allowing for the quantification of the $MV^{2+}$ concentration.

For streptavidin binding, fluorescence studies were performed to quantify the amount of streptavidin bound to the membrane surface. First, the functionalized nanotube membrane was incubated in 4 mL. Of fluorescein-isothiocyanate labeled streptavidin (streptavidin-FITC) solution for 6-8 h. The streptavidin-FITC solution was prepared by dissolving 1 mg of streptavidin-FITC in 4 mL. of Tris buffer. Fluorescence measurements were performed on a Fluorolog-2 spectrofluorometer (Jobin YVON-SPEX, Edison, N.J.), equipped with a 450-W xenon arc lamp using quartz cuvettes. The excitation wavelength was set at 498 nm, and emission was detected at 518 nm. For quantifying the amount of streptavidin-FITC, a calibration plot in the range 0.01 μg/mL (seven solutions) was used.

The present example demonstrated that nanoporous membranes fabricated in accordance with the present invention could be used to mimic ligand-gated ion channels by placing a selective molecule at the entrance of the CNT pore and reversibly coordinating it with a bulky receptor. This reversible binding of the ligand/receptor system leads to on/off switching of the pores. The desthiobiotin derivative bound reversibly to streptavidin. DSB-X™ biotin hydrazide was reacted with the carboxylate end groups of the CNT membrane using a carbodiimide-mediated reaction. FTIR studies were carried out to confirm the functionalization of the CNT membranes with of DSB-X™ biotin hydrazide. A peak at 1627 cm$^{-1}$ in the plasma oxidized CNT membrane was attributed to the C=O stretch of COOH. Expansion of the C=O stretch region for the DSB-functionalized membrane showed that the peak had broadened with the maximum still at 1627 cm$^{-1}$, and a shoulder at 1603 cm$^{-1}$, which can be assigned to the y c=o amide (I) and $\delta_{NH}$ amide (II) bands.

Binding of streptavidin to DSB-X™ biotin hydrazide functionalized CNT membrane was reversed in the presence of biotin at neutral pH, thus restoring the flux of the marker molecules across the channel. The affinity of streptavidin for desthiobiotin is known to be several orders of magnitude lower than that for biotin. Streptavidin bound to the desthiobiotin-functionalized membrane and blocked the pore. The bound streptavidin was released by incubating the membrane in a 1 mM solution of biotin in 50 mM Tris, 50 mM NaCl, pH 8.0 buffer. After releasing the bound streptavidin, the CNT membrane was washed with 50 mM Tris, 50 mM NaCl, pH 8.0 buffer solution three times, before evaluating its transport properties.

Figure 6:
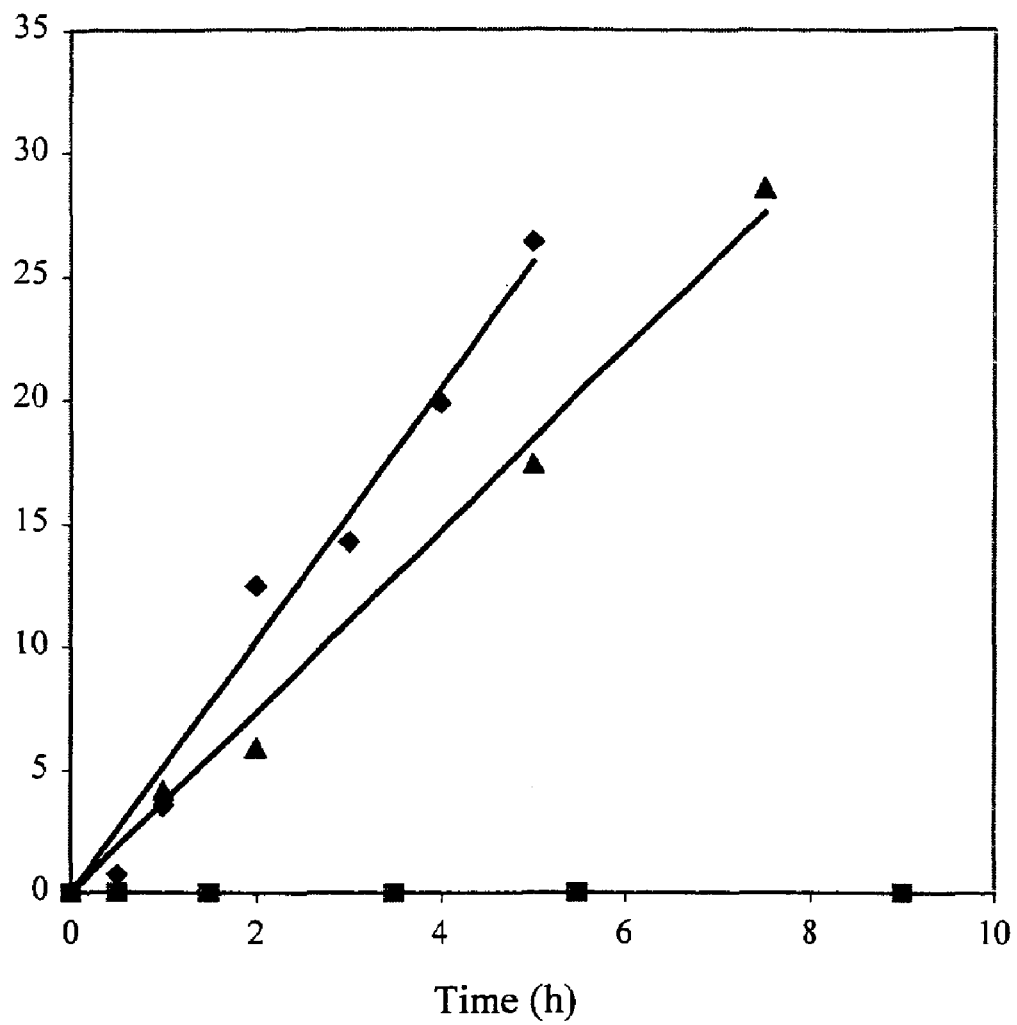
FIG. 6 shows flux data of methyl viologen through the pores of a CNT membrane (concentration of $MV^{2+}$ in the feed solution is 5 mM) (diamond symbol represents flux through the DSB-functionalized membrane, triangle symbol represents flux after biotin incubation, and square symbol represents flux after binding of streptavidin)

The opening and closing of the pores was detected by monitoring the transport of $MV^{2+}$ through the CNT cores across the membrane as shown in FIG. 6. Before the binding of streptavidin to the DSB-functionalized CNT membrane, a flux of 4.8 nmol cm$^{-2}$ h$^{-1}$ was observed for MV2+. A flux of 0.2 nmol cm$^{-2}$ h$^{-1}$ was observed after streptavidin binding. After incubating the streptavidin-coordinated membrane with biotin, streptavidin was released from the membrane, and a flux of 4.4. nmol cm$^{-2}$ h$^{-1}$ was restored. Thus, the binding of streptavidin was reversible, leading to a well-regulated transport through the membrane. Additionally, the transport of $Ru(bpy)_3^{2+}$ through the CNT cores across the membrane was also monitored. The ratio of the $MV^{2+}$/Ru$(bpy)_3^{2+}$ fluxes (found to be 1.5) through the DSB-functionalized CNT membrane was equal to the ratio of the corresponding diffusion coefficients in aqueous solution. This indicates that the pore size was large enough not to binder diffusion through the membrane. Indeed, the size of DSB molecule is very small (~1 nm) leaving at least a ~5-nm diameter at the entrance of the CNT core.

Fluorescence measurements were carried out to detect any remaining FITC-labeled streptavidin that remained bound to the nanotube membrane after exposure to a biotin containing solution. Estimates of the number of streptavidin molecules per pore and the area of membrane covered by streptavidin are shown in Table 1.

TABLE 1

Experimental and calculated values of streptavidin bound to DSB-X functionalized CNT membrane (Fluorescence studies).

| | |
|---|---|
| Surface area of membrane | 3.2 cm$^2$ |
| Areal density of CNTs | 6.0 × 10$^{10}$ CNTs/cm$^2$ |
| Amount of streptavidin | 0.267 + 0.017 μg |
| Streptavidin molecules/pore | 16.3 ± 0.8 |

An amount of 0.267±0.017 (n=3) μg of streptavidin was bound to the CNT membrane having a surface area of 3.2 cm$^2$. This corresponds to approximately 16 streptavidin molecules bound per pore using an estimated areal density of 6×10$^{10}$ CNTs/cm$^2$. This was expected since the nanotubes as fabricated are multiwalled, suggesting more than one binding site at each pore.

Additionally, because the tips of the CNTs extended beyond the membrane surface, side-wall modification by the plasma oxidation and subsequent DSB functionalization was possible. To support this hypothesis, the number of reactive sites onto which streptavidin could bind was estimated by decorating thiol functionalized CNTs with easily observed (by TEM) gold nanocrystals. For this, the polystyrene matrix of an as-prepared membrane was dissolved in toluene, and the multiwalled CNTs were modified with a reagent containing both a thiol and an amine (cystamine) instead of desthiobiotin, using the same carbodiimide reaction. These sites were then coordinated to nanocrystalline gold (5 mm diameter, similar to streptavidin volume). Of 16 multiwalled CNT tips analyzed by TEM, an average of 45 gold coordination sites per CNT were observed, which is consistent with the number of streptavidin molecules found to bind per DSB-functionalized CNT membrane. Given the structural differences of the two molecules used to modify the CNTs (DSB vs cystamine) this difference in the number of reactive sites is not unreasonable, considering the associated uncertainty in the areal density and efficiency of coupling.

Studies were also carried out to investigate whether there is physical adsorption of streptavidin onto the unfunctionalized CNT membrane, which could lead to blockage of the pores. For this, a CNT membrane was incubated in a streptavidin solution (1 mg/4 mL of Tris buffer) and shaken in a rotary shaker. The membrane was washed thrice with the buffer, and the flux measurements of $MV^{2+}$ and $Ru(bpy)_3^{2+}$ were carried out before and after incubation with streptavidin. The membrane maintained 95% transport flux for $MV^{2+}$ and 88% for $Ru(bpy)_3^{2+}$, indicating the absence of simple chemi/physiosorption leading to pore blockage. This observation was also implicit in the reversibility data shown in FIG. 6.

Another control experiment in support of ionic flux taking place through the cores of CNTs was also carried out because it has been recently reported under other multiwalled CNT growth conditions, that Fe nanocrystals could block multiwalled CNT cores in nitride membranes. Specifically, we performed the same membrane fabrication as described herein on a multiwalled CNT sample from an Fe-rich region of the deposition reactor, where nanotubes are blocked by Fe nanocrystals. The resultant composite membrane was the same as the working membranes described above (in term of polymer thickness and processing steps), except for the quality of multiwalled CNT cores, which were blocked. No flux of $Ru(bpy)_3^{2+}$ nor $MV^{2+}$ was seen after 32 h, indicating that diffusion through the polymer or other gross defects is insignificant. The detection limit of UV-vis analysis was experimentally found to be $5.2 \times 10^{-8}$ (M) corresponding to 0.2 nmol/cm$^2$ in FIG. 6. The conclusion that the observed flux in working membranes is through CNT cores was also consistent with the ability to gate transport with nm-scale biological molecules and $N_2$ desorption of pore size. Accordingly, the quality of the initial multiwalled CNTs is an important issue that does affect overall flux.

Summarizing, it was found that aligned carbon nanotube membranes could mimic biological ion channels by reversibly and selectively opening/closing pores in the presence of bioactive molecules. This approach can be broadly applied to other receptor/ligand pairs that can selectively block CNT core entrances. An important constraint is that the molecule bound to the CNT pore should be small enough (<~3 nm) to not block the core by itself. In this study, the pores of nanotube membranes could be reversibly opened and closed using the reversible binding of desthiobiotin to streptavidin. On/off states were obtained by binding and releasing of streptavidin from the DSB-functionalized tips of the CNT in the membrane. This was confirmed by ionic transport through the CNT core.

Example 5

This study focused on the effect of functional unit size, hydrophilicity and charge on the flux and relative selectivity of two similarly charged but differently sized molecules through CNT membranes. The flux characteristics of these analyte molecules have been studied in previous ordered nm-scale porous structures, thus allowing direct comparison to pore plating methods.

CNT membranes were fabricated using substantially the method of Example 1. The CNT membranes were functionalised using well known carbodiimide chemistry. The following chemicals were used for these reactions: 1-[3-(Dimethylamino)propyl]-3ethylcarbodiimide hydrochloride [EDC], Nonyl amine [(C9)], Direct Blue 71 [dye], 8-Amino caprylic acid [ACA], all from Aldrich. Kemamine P-298D, Crompton Corporation, USA [C22], MES (Sigma) buffer, Isopropyl alcohol (EMD; 99.5%), Ethyl alcohol (Aaper Alcohol and Chemical Co., Kentucky) were the other chemicals used. For reactions in water, D.I. water (~18 mΩ resistance) was used.

For the water soluble molecules, C9 and Direct Blue 71 dye, an appropriate amount of C9 and dye were added to 4 ml solution of 0.1 (M) MES buffer to make it 50 mM. 8 mg of EDC was dissolved in the solution and then the membrane was added to it. The reaction was carried out for 12 hours at ambient temperature, after which the membrane was washed with MES buffer and IPA to remove the excess reagents. These functionalised membranes was referred to as CNT-9 and CNT-dye.

Kemamine is a commercial fatty amine containing about 90% C22. It is insoluble in water, but soluble in IPA at 35° C. 32.36 mg of C22 & 8 mg of EDC was added to 4 ml of IPA along with the membrane and kept in water bathe at 35° C. The reaction was carried out for 12 hours and was washed with Ethyl alcohol. This functionalised membrane was referred to as CNT-22.

ACA is an 8 carbon atom molecule, containing terminal COOH and $NH_2$ groups. The membrane was first surface activated in 4 ml of 0.1 (M) MES by 8 mg of EDC and then added to 50 mM solution of ACA in 0.1 (M) MES buffer. Functionalisation was carried out in two steps, i.e. activation with EDC and then reaction of the activated COOH group with ACA, to avoid self reaction between the terminal COOH and $NH_2$ groups of ACA. These two steps were repeated four times to increase the spacer length and then finally functionalised with C9 according to the method described above. The membrane was washed with MES buffer and then with IPA. The functionalised membrane was termed CNT-40 (polypeptide). Tip functionalization molecular length was calculated by minimizing conformational energy using MM2 routine in Chemdraw.

For FTR studies of the functionalised membranes as described above, 2.5 mg of membrane was dissolved in 5 gm of toluene (Mallinckrodt, 100%), ultrasonicated for 5-10 minutes and then centrifuged 4-5 times to remove the dissolved polymer. The purified nanotubes in toluene were then mixed with FTIR grade KBr (Sigma-Aldrich, >99%), dried in vacuum oven for 12 hours at 25" Hg. As-received CNT's were scraped from the quartz substrate and similarly mixed and dried. The dried powder was then examined in ThermoNicolet Nexus 4700. FTIR spectra was analyzed after subtraction of KBr spectra from each.

Flux through the functionalised membranes was evaluated using a U-tube permeation experiment as described in Example 4. Liquids in the two chambers of the permeation set-up were maintained at the same level to avoid any pressure induced transport. Methyl viologen dichloride hydrate and Ruthenium bi-pyridine hexahydrate were purchased from Aldrich for use as probe molecules. The permeate was periodically pipetted out, the probe molecules quantified therein by UV-vis spectroscopy (HP 8543 Spectrophotometer) and the permeate was then transferred back to the chamber. $Ru(bpy)_3^{2+}$ has two peaks at wavelengths of 452 and 286 mm, whereas $MV^{+2}$ has a peak at 260 mm. The peak at 452 mm was used to quantify the amount of $Ru(bpy)_3^{2+}$. $MV^{+2}$ peak at 260 mm has interference from the amount of $Ru(bpy)_3^{2+}$, due to the peak at 286 mm. So, the contribution at 260 mm from the peak at 452 mm was deducted from the absorbance value at 260 mm and then used to quantify $MV^{+2}$. For quantifying the amounts of $Ru(bpy)_3^{2+}$ and $MV^{+2}$, calibration curves were determined by fitting non-linear (to account for the non-linear deviation from Lambert-Beer's Law in higher concentrations of analyte) curves to plots of absorbance vs. concentration of the analyte in the range $5*10^{-4}$ (M) to $1*10^{-6}$ (M).

Figure 7A:
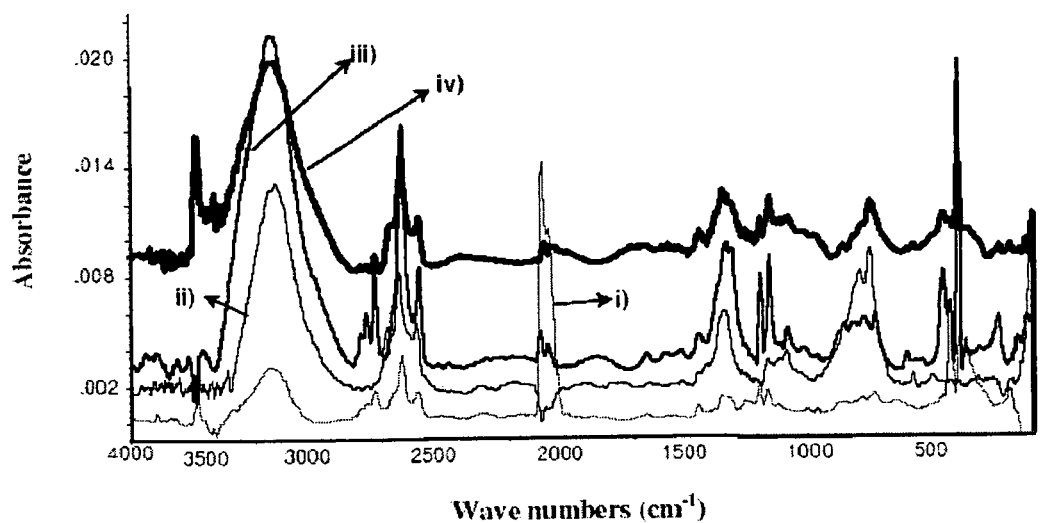
FIG. 7 depicts (a) FTIR spectra and (b) expanded and smoothed view of region of C=O stretch of (i) as-received CNTs, (ii) plasma oxidized CNT membrane, (iii) CNT-dye membrane, and (iv) CNT-9 membrane (the functionalized membranes show a peak at 1630 $cm^{-1}$ and a shoulder at 1600 $cm^{-1}$ indicative of amide (I) and amide (II) stretches)
Figure 7B:
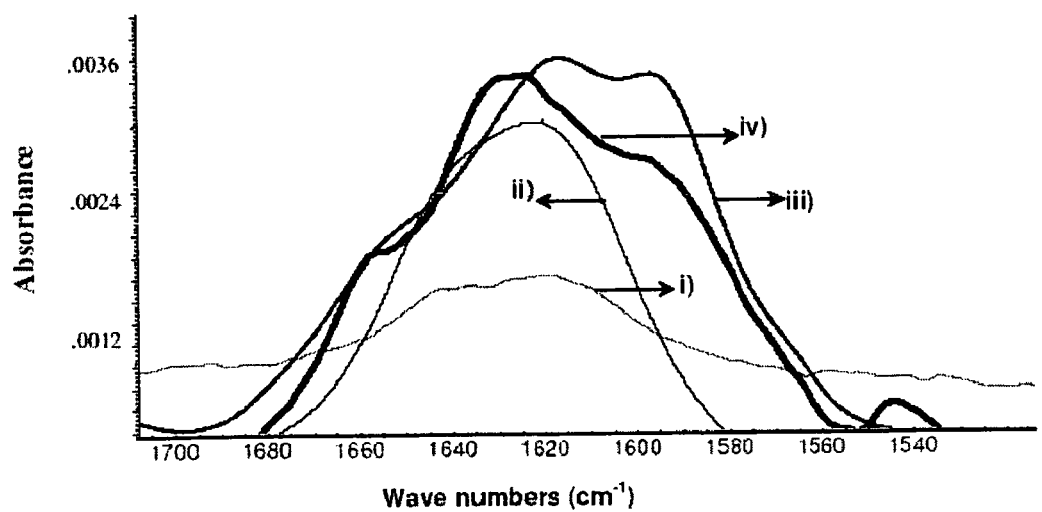

FTIR spectra of CVD grown as-received CNT, plasma oxidized CNT, CNT-dye and CNT-9, and expanded and smoothed view of the region of C=O stretch are shown in FIGS. 7*a* and 7*b* respectively. As received CNT did not show C=O stretch. In the case of plasma oxidized CNT, a peak at 1630 cm$^{-1}$ was found which can be attributed to C=O stretch in carboxylic acid. For chemically oxidized single walled carbon nanotubes, carbonyl stretch for carboxylic acid groups have been found in the range of 1700-1750 cm$^{-1}$, which was not observed in our case. Shift of C=O stretch to lower frequencies can occur when large aromatic groups are bound to it. Also noticed was the increase in the OH peak intensity at 3400-3500 cm$^{-1}$ for the plasma oxidized CNT and functionalised membranes compared to the as-received CNT, indicating formation of excess OH groups and consistent with the C=O stretch for carboxylic acid groups and phenol oxidation in plasma oxidation.

Peaks in the region 2800-3050 cm$^{-1}$ can be ascribed to C—H stretches from polystyrene, toluene or the functionalisation molecules. The peak at 1048 cm-1 is substituted benzene from polystyrene or toluene, both of which have similar IR signatures. The intensity of this peak increased in the plasma oxidized and functionalised membranes, showing that the purification process was not able to remove all polystyrene or toluene, adsorbed on or within the nanotubes. An expanded view of the region of C=O stretch for the functionalised membranes showed that the peak had broadened with the maximum at 1630 cm$^{-1}$ and a shoulder at 1600 cm$^{-1}$, (for CNT-dye) and 1604 cm$^{-1}$ (for CNT-9) whose intensity is less than the peak at 1630 cm$^{-1}$. They can be assigned $\gamma_{C=O}$ [amide (I)] and $\delta_{NH}$ [amide II] bands respectively. Thus, FTIR data clearly showed that there was a chemical functionalisation on the CNTs.

The effect of functional unit chain length on flux and selectivity was evaluated. Hindered diffusion occurs in membrane pores when the size of the permeating species is large enough allow to interaction with the pore walls. Molecules have been employed to study transport and hence probe the pore interiors in membranes. Transport of two molecules having similar charge but different size ($Ru(bpy)_3^{2+}$ and $MV^{+2}$) provided an indication of the relative hindrance provided by functional units at the entrance of CNT cores. Summary of the transport properties of the membranes are shown in Table 1.

TABLE 1

Summary of transport measurements across CNT membrane (0.3 cm$^2$ area, 5 mmol source).

| Membrane tip functionality | Size of Molecule (Ang.) | $MV^{+2}$ transport (nmoles/hr) (90% confidence) | $Ru(bpy)_3^{2+}$ Transport (nmoles/hr) (90% confidence) | α | Pure size calc. From alpha (Ang.) |
|---|---|---|---|---|---|
| CNT | 0 | 4.21 (±1.0) | 2.45 (±0.39) | 1.71 | — |
| CNT-9 | 11.4 | 6.40 (±2.18) | 2.12 (±0.90) | 3.02 | 40 |
| CNT-dye | 28 | 21.05 (+2.32) | 9.57 (±0.91) | 2.19 | 43 |
| CNT-22 | 26 | 1.84 (±0.48) | 0.93 (±0.22) | 1.98 | 32 |
| CNT-40 (polypeptide) | 52 | 0.649 (±0.13) | 0.178 (±0.023) | 3.64 | 32 |

The flux of permeate was calculated from linear fit of solute concentration vs. time. Experimental separation factor was determined for the membranes and pore size was calculated from the model using separation factor and hindered diffusion model at CNT entrance (model I).

The UV-vis measurements were not carried out in situ, that is not continuously using a U-tube permeation cell (as described above) as a UV-vis cell. Instead, the flux experiment was interrupted to analyze the entire volume of analyte cell. Due to time constraints of sequential analysis, each flux series have only 6-7 data points, causing a certain amount of uncertainty in predicting the flux rates (slope linear fit) from the measured values. Accordingly, along with the mean sample transport rate, the (±) uncertainty is shown at 90% confidence level. The (±) uncertainty is calculated from n, number of observations, t, student's t value at n−1 degrees of freedom and s, standard deviation of the measured values using the equation ts/n$^{0.5}$.

The ionic flux of $Ru(bpy)_3^{2+}$ calculated from membrane area (0.3 cm$^2$), areal density (6*10$^6$) and 7 nm pore diameter was found to be 0.35 μ-moles/cm$^2$-hr, comparable to fluxes of RU $(NH_3)_3^{3+}$ (0.9 μ-moles/cm$^2$-hr) in CNT membrane and benzonitrile in ordered alumina (0.3 μ-moles/cm$^2$-hr). The separation factor for CNT was 1.7, which is close to the ratio of their bulk diffusivity. Change in separation factor from that predicted by bulk diffusion coefficient, in the functionalised CNT membranes was proof of a membrane structure with the hollow core of CNT as the transport channel.

The separation factor increased to 3 in the CNT-9 membrane. Increase in separation factor is due to the decrease in pore size. Purely geometrical arguments, i.e. diameter of the CNT core (7 nm nominal)−2*length of the molecule would give a pore size of 47 A$^0$. When a longer aliphatic amine of length ~28 A$^0$, was attached to the CNT membrane (CNT-22), the selectivity declined to 1.98, but Ru-(bipy)$_3^{+2}$ permeability decreased 2.2 times compared to CNT-9. Separation factor was higher in CNT-9 than in CNT-22, despite attachment of a longer molecule. It is possible that the long hydrophobic alkyl chains, unlike in alumina or silica-based membranes, would prefer the horizontal surface of CNTs and not extend into the aqueous channel.

It is to be noted here that, the first three membranes evaluated (CNT, CNT-9, CNT-dye) were from a first batch and the next two (CNT-22, CNT-40) were from a different batch of membranes and fluxes from different batches cannot be directly compared. Fe-catalysed CVD process for synthesizing aligned carbon nanotube lead to the presence of iron nanoparticles in the CNT-cores causing batch to batch variation in membrane transport. Plasma oxidation and HCl treatment were used to remove iron particles, but in extreme cases they remain to affect the absolute flux values. However, the selectivity (i.e. the ratio of the transport rates of two species tested) was not affected by blocked CNTs.

We also evaluated the effect of water solubility and charge on flux and selectivity of the membranes. The dye molecule (CNT-dye) led to increased flow of positively charged species through the membrane (~4 times compared to the CNT membrane), indicating that there were electrostatic attractive forces acting on the positively charged permeate species by the negatively charged dye molecule. Along with an increase in flux, increase of separation factor in CNT-dye compared to CNT-22 was also observed despite the fact that dye molecule was slightly smaller than C-22. The presence of the charged functional unit did not lead to an increase in separation factor based on electrostatic attractions, because of the identical charges on $MV^{+2}$ and Ru(bi-py)$_3^{+2}$ Rather, it is believed that the effect was on the conformation of the charged, soluble molecule. Molecules in good solvents are entropically stable and tend to be in open position rather than a folded one, contributing to a larger decrease in pore size and hence increased separation factor. In CNT-40, a decrease in Ru-(bipy)$_3^{+2}$ flux (~5 times) compared to CNT-22 and enhancement in separation factor to 3.6 was observed. The long chain molecule is about 52 A$^0$ long and has hydrophilic peptide bond between them.

Thus, separation factor could be increased by attaching long chain, molecules containing hydrophilic bonds to the CNT. However, the separation factors do not increase significantly with the chain length, presumably because the molecules preferred to be in a horizontal rather than in vertical orientation to the carbon nanotube walls.

We also evaluated the solvent ionic strength effects on the CNT-dye membrane. The changes in separation factor and flux through CNT-dye in 0, 0.01 and 0.1 (M) KCl solutions are shown in Table 2.

TABLE 2

Transport measurement across CNT-dye in different concentration of electrolyte (KCl)

| Conditions | $MV^{+2}$ transport (90% confidence) | $Ru(bi-py)_3^{+2}$ Transport (90% confidence) | α |
|---|---|---|---|
| 0 (M) KCl | 21.05 (±2.32) | 9.57 (±0.91) | 2.19 |
| 0.01 (M) KCl | 8.88 (±0.4) | 3.24 (±0.17) | 2.74 |
| 0.1 (M) KCl | 10.36 (±0.97) | 4.12 (±0.275) | 2.51 |

About 3 times decrease in Ru-$(bipy)_3^{+2}$ flux in 0.01(M) KCl in comparison to the absence of electrolyte was observed. Decrease of flow of positively charged molecules in Nafion membranes have been attributed to a 'braking effect', which is an enhanced electrostatic attractive force between the positively charged analyte molecule and $SO_3^-$ groups on the membrane surface due to their close proximity. This 'braking effect' was found to occur in CNT-dye in the presence of an electrolyte, probably due to the polar groups of the functional unit coming closer to the analyte molecules transporting through the CNT cores. However, such electrostatic interactions should be equal for divalent cations, and hence should not lead to an increase in selectivity. But a modest increase in selectivity indicates that there is a pore size reduction effect as well. Increase in molecular interaction area in salt solutions due to dipolar coupling between the polar groups and ions have been reported in Langmuir/Langmuir-Blodgett films. Such interactions will be prominent in the charged dye molecule leading to a conformational changes with concomitant decrease in pore size, explaining the observed decrease in flux and increase in selectivity. It is known that diffusion of solutes in pores is hindered by the pore and its wall. Two correction factors are used to model this phenomena, both of which are a function of reduced pore diameter, γ, given by:

$$\gamma = \text{solute molecule diameter/pore diameter} \quad (1)$$

Hindered diffusion becomes dominant when ẽ approaches 1 for γ>1, solute exclusion occurs. Hindered diffusivity, $D_h$ can be written as:

$$D_h = D_0(1-\gamma)^2(1-2.104\gamma+2.09\gamma^3-0.95\gamma^5) \quad (2)$$

where $D_0$ is the bulk diffusivity. The second term in the equation is the stearic partition co-efficient and the third is hydrodynamic hindrance factor. We assume that the presence of long chain molecules inside the nanotube would hinder the diffusion of the permeating species.

Two models were considered (i) hindered diffusion only at distances $L_1/2$ at the two ends of the CNT and normal diffusion along the length $L_2$, the total length of the nanotube is thus $L_1+L_2$ (ii) hindered diffusion throughout the nanotube. We assumed steady state conditions for this model. Since the cross-sectional area inside the nanotube is changing, W=N.A is constant, where N is the molecular flux (moles/$cm^2$-hr) and A is the pore area ($cm^2$). We also assumed that the concentration of a species changed along the nanotube, being $C_1$ (moles/$cm^3$) at the entrance and $C_4$ (moles/$cm^3$) at the exit which are same as the feed and permeate concentration respectively. $C_2$ (moles/$cm^3$) and $C_3$ (moles/$cm^3$) being the concentrations at the end of the first functional layer at the entrance and at the beginning of the second functional layer at the exit. The cross sectional area of non-functionalised nanotube is $A_0$ ($cm^2$) and the area where hindered diffusion occurs is $A_h$ ($cm^2$) and are given by:

$$A_0 = \pi d_0^2/4; \quad A_h = \pi d_p^2/4 \quad (3)$$

where $d_0$ is the diameter ($A^0$) of the inner core of the nanotube and $d_p$ is the pore diameter ($A^0$) at the entrance and exit. Thus:

$$W = -D_h A_h (C_1-C_2)/0.5 L_1 = -D_0 A_0 (C_2-C_3)/L_2 = -D_h A_h (C_3-C_4)/0.5 L_1 = -(C_1-C_2)/(0.5 L_1/D_h A_h) = -(C_2-C_3)/(L_2/D_0 A_0) = -(C_3-C_4)/(0.5 L_1/D_h A_h) = -(C_1-C_4)/(L_1/D_h A_h + L_2/D_0 A_0) \quad (4)$$

For two different molecules, the following separation factor (α) is proposed:

$$\alpha = (L_1/D_{h,2} A_h + L_2/D_{0,2} A_0)/(L_1/D_{h,1} A_h + L_2/D_{0,1} A_0) \quad (5)$$

This equation can be simplified for case (ii) in which $L_2=0$, thus $$\alpha = D_{h,1}/D_{h,2} \quad (6)$$

For the probe molecules, Ruthenium bi-pyridine is a spherical molecule with diameter about 11.8 $A^0$, $MV^{+2}$ is a cylindrical molecule with length 11 $A^0$ and breadth 3.3 $A^0$. The equivalent spherical diameter for the molecule is about 5.2 $A^0$. Thus, reduced pore diameter for each species can be found out as a function of $d_p$. The bulk diffusivity of Ru-$(bipy)_3^{+2}$ is $5.16*10^{-6}$ $cm^2$/s.[1] The bulk diffusivity of $MV^{+2}$ is 1.5 times that of Ru-$(bipy)_3^{+2}$. Experiments were carried out to determine the length up to which the nanotubes were oxidized. The carbon nanotube membrane was dissolved in toluene and centrifuged to remove most of the polymer. Thereafter, the nanotubes were functionalized with 2-Aminoethanethiol using carbodiimide chemistry and finally decorated with gold nano-particles (10.nm diameter) by covalent linkage with the thiol group of 2-Aminoethanethiol. Quantitative estimates of nanoparticle density obtained from 30 different CNT's of 10 μm length, showed that the average nanoparticle density decreases from 526 particles/micron at the tips to negligible (<7 particles/micron) at location of 700 nm from the carbon nanotube tips. Thus, the carbon nanotubes were functionalised at each end only up to a distance ~7% of the total length of the nanotube. Though the exterior of the CNT's were decorated with Au particles, it is reasonable to assume that the same would happen in the inside during functionalization with molecules. Thus, $L_1$~14% and $L_2$~86% of the total length of the nanotubes.

Considering hindered diffusion all along the pore length gives much higher separation factors and does not fit well with our experimental data. However, the pore size of the different membranes can be found out from the experimental separation factors obtained using the first model. Pore sizes calculated from this model for the differently functionalised membrane are shown in Table 1. As discussed earlier, pore size reduction would be dependent upon the solvation and also orientation of the molecule, e.g., the 5.5 nm long polypeptide molecule should geometrically block the pores completely. However, a pore size of 3.4 nm is obtained from the model. Since the molecule contains hydrophilic peptide bonds, it should be solvated. Hence, one can infer that the long chain molecules prefer a horizontal orientation along the walls of the carbon nanotube.

Summarizing, the hollow inner hydrophobic cores of the CNTs in the composite structure allowed ionic transport. Further, chemical functionalization at CNT core entrances in aligned CNT membranes enhanced separation/pore size reduction in carbon nanotube membranes as chain length and solubility of the functional units increased. Hydrophobic interactions with the walls of the nanotube played an important role, such that long alkyl chains that contain hydrophilic peptide bonds between them also preferring a horizontal rather than a vertical orientation to the walls of the nanotube. The presence of charged molecules at the entrance to the CNT cores increased the flux of positively charged cations. Conformation of charged molecules placed at the CNT entrance in electrolytic solutions can altered flux and led to higher separation factors.

Example 6

A CNT membrane was prepared substantially as described in Example 1. Briefly, an aligned array of MWCNTs Was grown by chemical vapor deposition using ferrocene/xylene feed gas. The volume between the CNTs was filled with polystyrene and the composite film was removed from the quartz substrate. Excess surface polymer, as well as Fe nanocrystals at the CNT tips, were removed by $H_2O$-plasma oxidation. This resulted in MWCNTs traversing the polystyrene film with carboxylic (—COOH) group functionalization at the CNT tips.

Figure 8A:
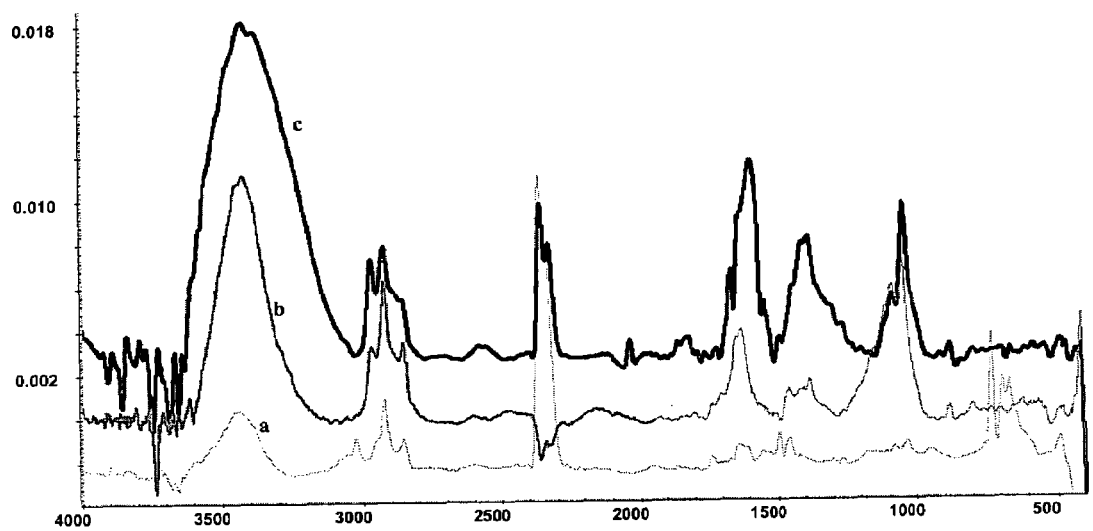
FIG. 8 depicts (a) FTIR spectra of CNTs at various stages of functionalization, and (b) expanded FTIR spectra of carbonyl-stretch region (1500-1700 $cm^{-1}$) at various stages of CNT functionalization.
Figure 8B:
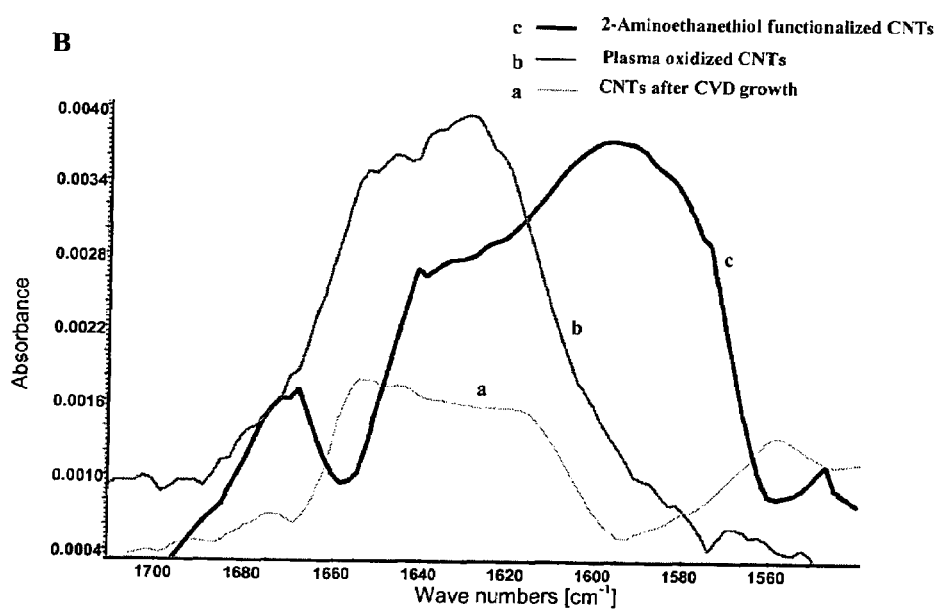

For observing the chemistry at the CNT tips, the polystyrene-CNT composite was dissolved in toluene and rinsed several times to obtain a clean suspension of CNTs. Using 1-ethyl-3-[3-dimethyl aminopropyl]carbodiimide hydrochloride (EDC) as linker in pH 4 buffer solution and water as reaction medium, carboxylic acid-terminated CNT tips were thiol-derivatized with 2-aminoethanethiol [$H_2N$—$(CH_2)_2$—SH]. Chemical derivatization of suspended CNTs (without a polystyrene matrix) was confirmed by Fourier-transform infrared (FTIR) studies, as shown in FIGS. 8a-8b. FT-IR spectra were compared for: a) CVD-grown CNTs, b) CNTs obtained after dissolution of a plasma and acid-oxidized CNT membrane, and c) 2-aminoethanethiol-functionalized CNTs.

As expected, plasma oxidation resulted in an increase of carbonyl and O—H stretches. 2-Aminoethanethiol derivatization resulted in the broad C—H stretches and A shift in the location of the carbonyl peak. Of most interest were the carbonyl groups (FIG. 8b), as the as-received CVD-grown CNTs did not show a carbonyl stretch. However, in the case of plasma-oxidized CNTs obtained after membrane dissolution, a carbonyl peak was apparent at 1630 $cm^{-1}$ (dotted line in FIG. 8a), attributed to the carboxylic acid (—COOH) group. Interference from oxidized polystyrene was not expected owing to the extensive cleaning process to dissolve the polymer film and suspend the MWCNTs. FIG. 8a also shows the increase in the O—H peak intensity at 3400-3500 $cm^{-1}$ for the plasma-oxidized CNTs and 2-aminoethanethiol-functionalized CNTs, compared to the as-received CNTS. This indicated the formation of excess hydroxyl groups, which is consistent with carboxylic and phenol groups resulting from plasma oxidation. However, $H_2O$ absorption in a KBr pellet makes this trend difficult to quantify. Expansion of the carbonyl region (FIG. 8b and dotted lines in FIG. 8a) for the CNTs showed a shoulder at 1590 $cm^{-1}$ indicative of amide-bond formation. A shoulder at 1630 $cm^{-1}$ remained, indicating that not all carbonyl groups were derivatized. Peaks in the range of 2800-3050 $cm^{-1}$ (aromatic C—H stretch) (FIG. 2A) could be attributed to toluene solvent. However, it is difficult to differentiate between polystyrene and toluene as they have similar IR signatures.

An attempt was made to determine sulfur in 2-aminoethanethiol-functionalized CNTs using a energy-dispersive X-ray spectroscopy (EDX) study in analytical transmission electron microscopy (TEM). Carbon deposition and the resolution of the EDX detector (~1%) made it difficult to detect a monolayer of 2-aminoethanethiol-functionalized on the CNT tips.

Figure 9:
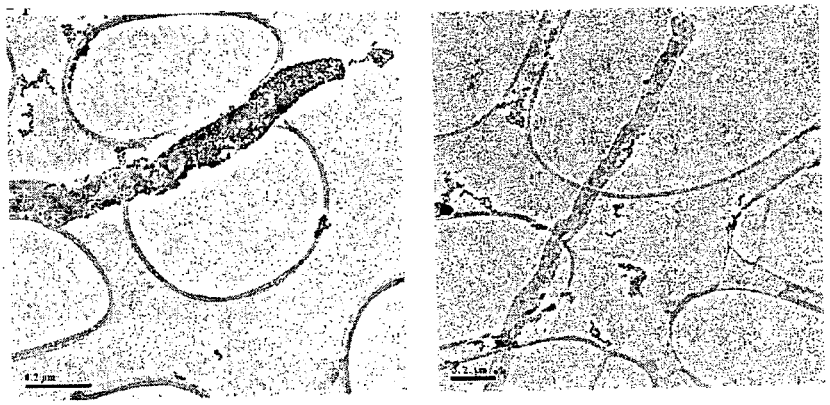
FIG. 9 is a TEM micrograph showing a thiol-functionalized CNT tip decorated with gold nanoparticles, with minimal sidewall functionalization (scale bar=100 nm)

FTIR studies cannot measure the spatial distribution of the functionalized groups, but are supportive methods for confirmed the presence of functionalized groups can be observed via gold-nanoparticle decoration of thiol functional groups on the CNTs. Gold nanoparticles can be easily covalently linked to thiol-terminated molecules and can be conveniently observed with electron microscopy to demonstrate the presence of the functional group. In the process reported here, the functionalization and dissolution process did not involve any polyelectrolyte, and the interaction of CNTs with gold nanoparticles was through covalent Au—S Bonding. The TEM images in FIG. 9 showed a high-density of gold nanoparticles at the CNT tips, indicating of selective functionalization of the CNT ends. Also observed in TEM images (FIG. 9) was that the CNTs, after dissolution and cleaning processes, were free from the polymer which initially protected the CNT sidewalls from oxidation. An observable amount of sidewall functionalization could be attributed to the presence of defects created during the growth of the CNTs (ultrasonication of CNTs during cleaning and dispersion processes) or physisorption during the final rinsing step.

Strong solution-based oxidation treatment uncontrollably attacks the CNT surface and cuts them so they are shorter. Suspension of MWCNTs are partially susceptible to sidewall functionalization during solution-based oxidation, since the outer layers can be oxidized without completely cutting the entire tube. Because the sidewalls are protected by polystyrene during the oxidation process, almost the original length of the CNTs (~5-10 μm), determined by the membrane thickness, was maintained.

Figure 10:
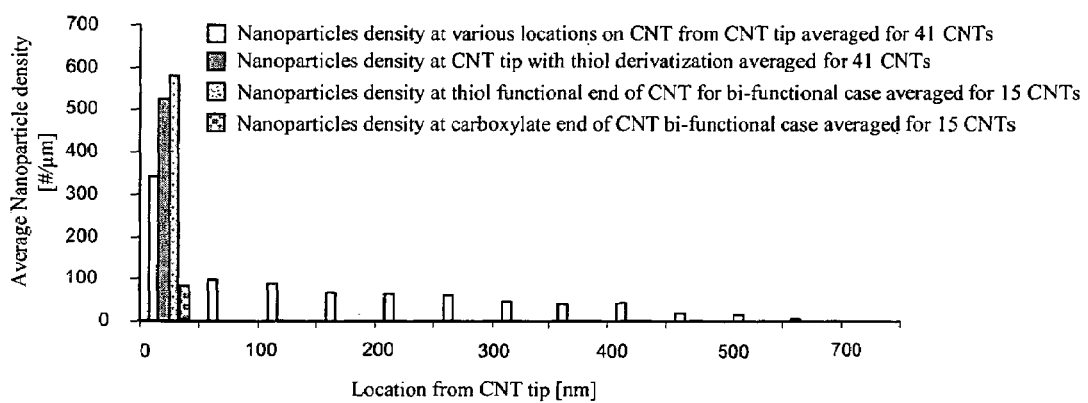
FIG. 10 shows a histogram of estimates of average nanoparticle density versus distance from a CNT tip, extrapolated from TEM observations.

An estimate of nanoparticle density can be obtained from TEM images by counting the number of Au nanoparticles (10 nm diameter) seen along a given length of a CNT. This observation was made for more than thirty different CNTs and the average nanoparticle density is shown in the histogram of FIG. 10. The density [particles (μm length)$^{-1}$] decreased from ~529 particles $\mu m^{-1}$ (in the first ~34 nm of CNT length), to negligible values (<7 particles $\mu m^{-1}$) at a location beyond 700 nm from the tip. Because polystyrene etches faster than CNTs in the plasma oxidation of membranes, the tips of the CNTs were observed to be slightly above the polymer film. Therefore, a small portion of the CNT sidewall on both sides of the membrane was exposed to oxidation.

For an average length of 34 nm, starting form the CNT tip, the average nanoparticle coverage (ratio of total projection area of nanoparticles to total surface area of sidewall exposed to oxidation) is approximately ~20%. The average coverage (ratio of total projection area of nanoparticles to total surface area at tips) at the CNT tips is approximately 52%. With 10 nm-diameter nano-crystalline Au (nc-Au), the maximum functionality detectable at saturation (i.e., 100% coverage) is $10^{12}$ (reactive sites) $cm^{-2}$. From nc-Au coverage, an estimate of surface functionality is $5 \times 10^{11}$ sites $cm^{-2}$ at the tips and $2 \times 10^{11}$ sites $cm^{-2}$ along the sidewalls of the CNTs above the polystyrene matrix. Multiple reactive sites can be under the nc-Au, so this TEM observation is a lower-limit estimate of actual thiol functionality. As a reference, the density of broken carbon bonds at the edge of cleaved graphite and density of graphite rings on a surface are $1.5 \times 10^{15}$ and $3.5 \times 10^{15}$ $cm^{-2}$, respectively. On average, it appeared that a small percentage of all possible carbon atoms at the tips and exposed CNT sidewalls were thiol-functionalized. Since functional coverage was relatively low (several of the thiol molecules tethered per nanoparticle), we did not see evidence that the nc-Au is bound strongly enough to the CNT surface to experience significant stress. Though ~30 nm of a MWCNT was above the polystyrene matrix (and thus subject to sidewall oxidation), it is possible to selectively electrochemically oxidize only the conductive CNT down into the insulating polystyrene matrix. This results in selective functionalization of the etched MWCNTs only at the tips, since no CNT sidewall would be exposed above the polystyrene matrix to an oxidative solution.

Figure 11:
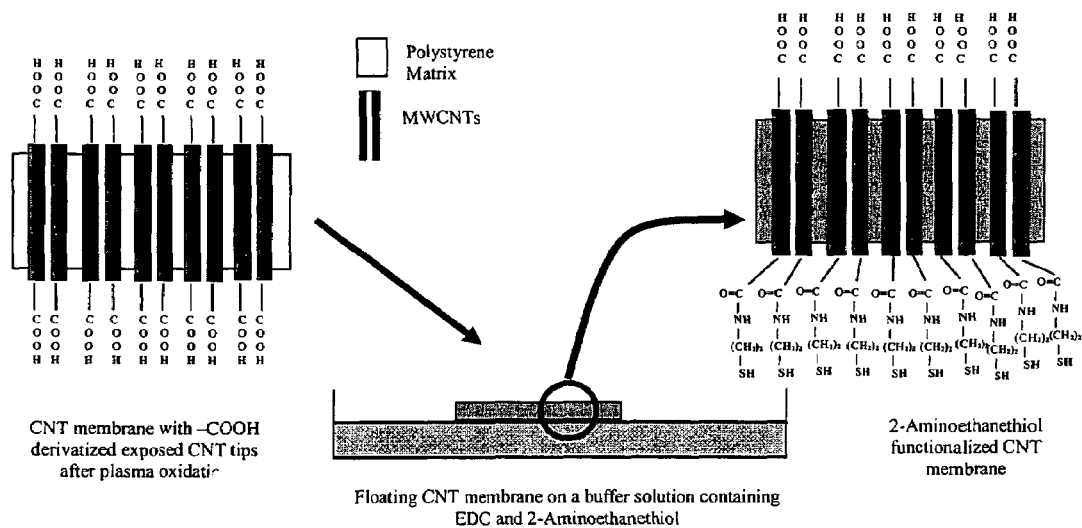
FIG. 11 schematically depicts a functionalization scheme for a plasma-oxidized CNT membrane (shown in cross-section) by floating on a buffer solution containing EDC and 2-aminoethanethiol, resulting in bifunctional CNTs in the membrane structure.

Using MWCNT membranes, it is possible to functionalise only one side of a membrane by floating the membrane on top of a reactive solution of 2-aminoethanethiol and EDC linker. The hydrophobic nature of polystyrene allows sufficient surface tension to float the membrane on top of the aqueous solution. This approach, allowing exposed CNT tips on only one side of membrane to come into contact with functionalizing solution, is shown schematically in FIG. 11.

Dissolution of such a membrane in toluene results in a suspension of bifunctional MWCNTs. Bifunctional in this case means that CNTs have different functional chemistry (thiol or carboxyl) at each end of the CNT. To monitor this bifunctional character, a colloidal gold-nanoparticle solution was added to an ethanolic solution of bifunctional CNTs. Gold-nanoparticle decoration occurred at the thiol-derivatized end of the CNTs, while the carboxyl end had only background amounts. This was consistently observed in TEM images (not shown). FIG. 10 includes the histogram of fifteen different CNTs with selective thiol or carboxylate functionality near the CNT tip. The thiol-functionalized end had an estimated nanoparticle density of ~580 $\mu m^{-1}$ on an average length of ~44 nm starting from the CNT tip. The carboxyl-functionalized MWCNT end had an average nanoparticle density of ~80 nanoparticles $\mu m^{-1}$, which is the same density as for non-derivatized sidewalls.

Aligned MWCNT membranes could be utilized to selectively functionalize each end of MWCNTs. During the oxidation process, CNT sidewalls were protected by a continuous polystyrene matrix, resulting in negligible sidewall functionalization. The presence of functionalized groups on CNTs was further confirmed by FTIR studies. The spatial location of thiol-derivatized CNT ends were readily observed using TEM by the covalent attachment of gold nanoparticles. Dissolution of the polystyrene matrix resulted in a suspension of MWCNTs with each end having a different chemical functionality. Such controlled functionalization processes could be used to create self-directed patterned architectures.

Example 7

In the gate-keeper scheme as discussed in the previous examples, the pore entrance has a highly selective chemical receptor that attracts a target molecule which is either displaced by another target molecule or has a high probability of being released into the pore. Other similarly sized molecules that do not selectively bind to the receptor would be expelled away from the membrane due to steric hindrance. The practical advantage to a gate-keeper approach is that it is possible to have high flux and high chemical selectivity. A membrane comprising an aligned array of CNTs as discussed supra is an ideal structure for such a gate-keeper scheme in the context of defending against chemical warfare (CW) agents.

Figure 12:
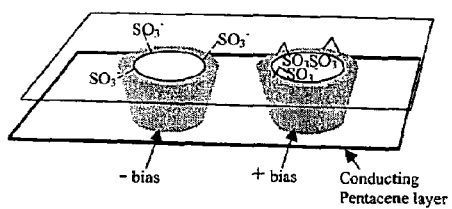
FIG. 12 shows schematically alteration of pore size inside a CNT by applied bias.

The most important aspect of this proposed membrane system is that the carboxylic group-containing ends of CNTs (from the oxidation treatment) can be further functionalized. Moreover, this chemical functionalization occurs at the ends of the tubes allowing the molecule to serve as a gate keeper for the membrane structure. One novel approach is shown in FIG. 12, in which a charged sulfonate group (such as 2-(n-(3-aminophenyl)-n-methylsulfamoyl) ethyl sulfate) is attached to the end of the tube. Applied potential would result in ion exchange of the ion. Thus the group can be brought in or out of the inner diameter by applied bias. This results in a "smart" material that can be opened or closed depending on the threat condition. This geometry requires the polymer to be an insulator so that the charge is localized in the CNT. This proposed structure is unique in having a conducting pore path, but an overall insulating structure.

Figure 13:
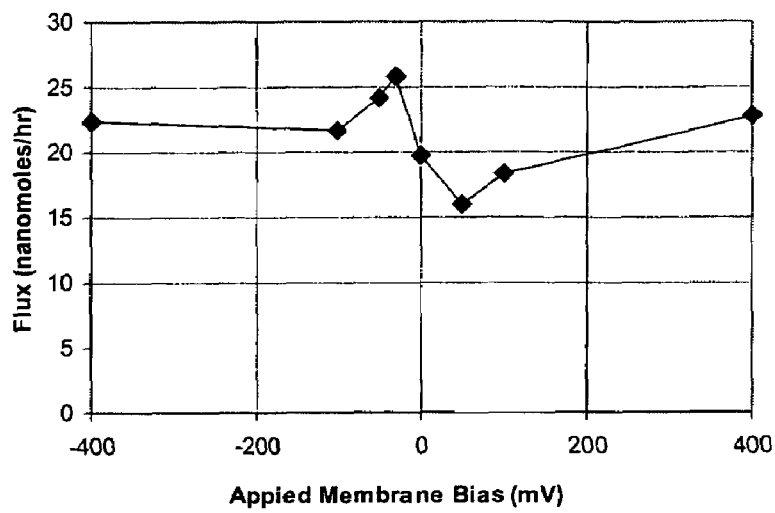
FIG. 13 illustrates transport of methylviologen$^{2+}$ across a CNT-dye membrane, functionalized with two polypeptide links (2 nm in length) and anionic dye molecule, as a function of an applied bias.

To demonstrate this function, a CNT-dye membrane (0.3 $cm^2$ area) fabricated as described in Example 5 was subjected to an applied bias. The CNT tips were functionalized with anionic dye as described, and also with 2 polypeptide links (2 nm long). Passage of methylviologen$^{2+}$ was quantified in a U-tube permeation experiment as previously described by UV-vis absorption. The reference electrode was a standard Ag/AgCl. Both the permeate and the feed solutions included 0.1 M KCl electrolyte solution. As shown in FIG. 13, application of a bias across the membrane affected $MV^{2+}$ flux.

Figure 14:
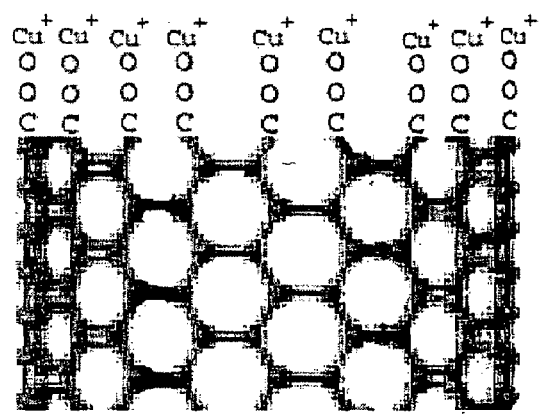
FIG. 14 schematically depicts coordinated $Cu^+$ at carboxylic functionalized CNT ends.

Another approach is to have the CW agent decompose at the pore entrance. There is long history of Cu being used to decompose phosphonate based nerve agents such as Sarin and its analog DFP (Diisopropyl fluorophosphate). In the catalytic reaction, water vapor would be provided by the perspiration of the individual. A novel approach presented here is to coordinate Cu to carboxylic ends of CNTs, forcing passing chemical agents to interact. This is schematically seen in FIG. 14. Further enhancement of decomposition kinetics results due to high effective concentration of forcing Sarin analog in close proximity. The solution measured kinetic rate of 0.01/molS would be nearly instantaneous on the $nm^3$-scale volume involved. Also the hydrophobic nature of the nanotubule pore would encourage the polar Sarin analog molecule to stay coordinated with the ionic catalyst, further enhancing reaction rate. Importantly we can readily quantify the concentration of any unreacted DFP passing through the membrane electrochemically. Reaction rates can be quantified by total volume flux and analyte concentration.

The foregoing description of the preferred embodiment of this invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for producing a permeable membrane, comprising the steps of:
    aligning a plurality of hollow nanotubules to form a mat;
    coating the mat with a continuous polymer matrix to form a membrane; and
    etching the membrane to remove a layer of polymer from a surface of the membrane to (a) open the plurality of hollow nanotubules whereby the nanotubules define pores passing through the membrane, and (b) oxidize an end of the nanotubules to form carboxylate groups.

2. The method of claim 1, wherein each of the plurality of nanotubules includes a hydrophobic lumen.

3. The method of claim 1, wherein the nanotubules are selected from the group consisting of multi-walled carbon nanotubes, single-walled carbon nanotubes, self-assembling macromolecular tubules comprising peptides and porphyrins, and any mixture thereof.

4. The method of claim 3, wherein the aligned hollow nanotubules are assembled in situ on a substrate.

5. The method of claim 4, wherein the aligned nanotubules are removed from the substrate after coating with the polymer matrix.

6. The method of claim 1, wherein the polymer matrix is selected from the group consisting of a thermoset resin, a soluble cast polymer, a castable solidifying sol-gel solution, and any combination thereof.

7. The method of claim 6, wherein the polymer matrix is selected from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

8. The method of claim 7, wherein the aligned nanotubule mat is coated by dissolving the polymer matrix in a suitable solvent, followed by spin-coating or high flow velocity rinsing of the mat with the polymer-solvent mix.

9. The method of claim 1, wherein the step of etching the membrane is performed using an oxidative method selected from the group consisting of plasma oxidation, electrochemical oxidation, anodic oxidation, exposure to an oxidizing acid, exposure to ozone, exposure to peroxide, exposure to permanganate, and any combination thereof.

10. The method of claim 9, wherein the membrane is selectively etched whereby the plurality of nanotubules are shortened to a length that is less than a dimension of the polymer matrix.

11. The method of claim 10, wherein the membrane is selectively etched by electrochemical oxidation.

12. The method of claim 1, further including the step of binding at least one additional functional unit to the carboxylate groups.

13. The method of claim 12, including selecting the at least one additional functional unit to include at least one available amine group to bind the at least one additional functional unit to the nanotubule end carboxylate group.

14. The method of claim 13, wherein the at least one additional functional unit is adapted to selectively open or at least partially occlude the pore of an adjacent nanotubule.

15. The method of claim 14, including selecting the at least one additional functional unit from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof.

16. The method of claim 15, including selecting the at least one additional functional unit from the group consisting of biotin, avidin, streptavidin, aliphatic amines, charged dyes, anionically charged ligands, cationically charged ligands, and any combination thereof.

17. The method of claim 14, wherein the at least one additional functional unit changes conformation to selectively expose or to at least partially occlude the pore of the adjacent nanotubule in response to an application of an electrical impulse to the membrane.

18. The method of claim 17, wherein the at least one additional functional unit is Direct Blue dye 71.

19. An ordered nanoporous permeable membrane, comprising a plurality of aligned hollow nanotubules coated with a continuous polymer matrix to form a membrane, wherein the membrane is etched to remove a layer of polymer from a surface of the membrane to (a) open the plurality of hollow nanotubules whereby the nanotubules define pores passing through the membrane, and (b) oxidize an end of the nanotubules to form carboxylate groups.

20. The membrane of claim 19, wherein each of the plurality of nanotubules includes a hydrophobic lumen.

21. The membrane of claim 19, wherein the nanotubules are selected from the group consisting of multi-walled carbon nanotubes, single-walled carbon nanotubes, self-assembling macromolecular tubules comprising peptides and porphyrins, and any mixture thereof.

22. The membrane of claim 21, wherein the aligned hollow nanotubules are assembled in situ on a substrate.

23. The membrane of claim 22, wherein the aligned nanotubules are removed from the substrate after coating with the polymer matrix.

24. The membrane of claim 19, wherein the polymer matrix is selected from the group consisting of a thermoset resin, a soluble cast polymer, a castable solidifying sol-gel solution, and any combination thereof.

25. The membrane of claim 24, wherein the polymer matrix is selected from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

26. The membrane of claim 19, wherein an oxidative method selected from the group consisting of plasma oxidation, electrochemical oxidation, anodic oxidation, exposure to an oxidizing acid, exposure to ozone, exposure to peroxide, exposure to permanganate, and any combination thereof is used to etch the polymer matrix.

27. The membrane of claim 26, wherein the membrane is selectively etched whereby the plurality of nanotubules are shortened to a length that is less than a dimension of the polymer matrix.

28. The membrane of claim 27, wherein the membrane is selectively etched by electrochemical oxidation.

29. The membrane of claim 19, further including at least one additional functional unit bound to the carboxylate groups.

30. The membrane of claim 29, wherein the at least one additional functional unit includes at least one available amine group to bind the at least one additional functional unit to the nanotubule end carboxylate group.

31. The membrane of claim 30, wherein the at least one additional functional unit is adapted to selectively open or to at least partially occlude the pore of an adjacent nanotubule.

32. The membrane of claim 31, wherein the at least one additional functional unit is selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof.

33. The membrane of claim 32, wherein the at least one additional functional unit is selected from the group consisting of biotin, avidin, streptavidin, aliphatic amines, charged dyes, anionically charged ligands, cationically charged ligands, and any combination thereof.

34. The membrane of claim 31, wherein the at least one additional functional unit changes conformation to selectively expose or to at least partially occlude the pore of the adjacent nanotubule in response to an application of an electrical impulse to the membrane.

35. The membrane of claim 34, wherein the at least one additional functional unit is Direct Blue Dye 71.

36. A method for altering flux of a target molecule through an ordered nanoporous permeable membrane, comprising:
aligning a plurality of hollow nanotubules to form a mat;
coating the mat with a continuous polymer matrix to form a membrane;
etching the membrane to remove a layer of polymer from a surface of the membrane to (a) open the plurality of hollow nanotubules whereby the nanotubules define pores passing through the membrane, and (b) oxidize an end of the nanotubules to form carboxylate groups; and
binding at least one additional functional unit to the carboxylate groups to alter a flux rate of a predetermined target molecule through the permeable membrane.

37. The method of claim 36, wherein the aligned nanotubule mat is coated by dissolving the polymer matrix in a suitable solvent, followed by spin-coating or high flow velocity rinsing of the mat with the polymer-solvent mix.

38. The method of claim 36, including selecting the at least one additional functional unit to include at least one available amine group to bind the at least one additional functional unit to the nanotubule end carboxylate group.

39. The method of claim 38, wherein the at least one additional functional unit is adapted to selectively open or at least partially occlude the pore of an adjacent nanotubule.

40. The method of claim 36, including selecting the at least one additional functional unit from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof.

41. The method of claim 40, including selecting the at least one additional functional unit from the group consisting of biotin, avidin, streptavidin, aliphatic amines, charged dyes, anionically charged ligands, cationically charged ligands, and any combination thereof.

42. The method of claim 36, wherein the at least one additional functional unit changes conformation to selectively expose or to at least partially occlude the pore of the adjacent nanotubule in response to an application of an electrical impulse to the membrane.

43. The method of claim 42, wherein the at least one additional functional unit is Direct Blue Dye 71.

44. The method of claim 36, wherein the at least one additional functional unit reversibly binds to the target molecule.

45. The method of claim 44, further including the step of adding a displacing molecule which displaces the reversibly bound target molecule from the at least one additional functional unit.

46. The method of claim 36, wherein flux of a target molecule is altered by at least partially occluding the pore of the adjacent nanotubule to a predetermined degree.

47. The method of claim 46, wherein the step of at least partially occluding the pore of the adjacent nanotubule is achieved by selecting the at least one additional functional unit having a length suitable to occlude the pore of the adjacent nanotubule to the predetermined degree.

48. The method of claim 47, wherein the step of occluding the pore of the adjacent nanotubule to the predetermined degree is achieved by adding a predetermined number of spacer molecules to the at least one additional functional unit to alter a length thereof.

49. The method of claim 36, wherein flux of a target molecule is altered by selecting as the at least one additional functional unit a molecule which changes conformation to expose or to at least partially occlude the pore of the adjacent nanotubule in response to an application of an electrical impulse to the membrane.

50. The method of claim 49, wherein the at least one additional functional unit is Direct Blue Dye 71.

51. A method for increasing flux of a target molecule through an ordered, nanoporous permeable membrane, comprising:
aligning a plurality of hollow nanotubules to form a mat;
coating the mat with a continuous polymer matrix to form a membrane; and
selectively etching the membrane to remove a layer of polymer from a surface of the membrane to (a) open the plurality of hollow nanotubules whereby the nanotubules define pores passing through the membrane, and (b) oxidize an end of the nanotubules to form carboxylate groups;
the step of selectively etching the membrane being performed whereby the plurality of nanotubules are shortened to a length that is less than a dimension of the polymer matrix, providing a path for flux of the target molecule that is less than the dimension of the polymer matrix.

52. The method of claim 51, including selecting the nanotubules from the group consisting of multi-walled carbon nanotubes, single-walled carbon nanotubes, self-assembling macromolecular tubules comprising peptides and porphyrins, and any mixture thereof.

53. The method of claim 51, including selecting the polymer matrix from the group consisting of a thermoset resin, a soluble cast polymer, a castable solidifying sol-gel solution, and any combination thereof.

54. The method of claim 53, including selecting the polymer matrix from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

55. The method of claim 54, including coating the aligned nanotubule mat by dissolving the polymer matrix in a suitable solvent, followed by spin-coating or high flow velocity rinsing of the mat with the polymer-solvent mix.

56. The method of claim 51, wherein the step of selectively etching the membrane is performed by electrochemical oxidation.

57. The method of claim 51, further including the step of binding at least one additional functional unit to the carboxylate groups.

58. The method of claim 57, including selecting the at least one additional functional unit to include at least one available amine group to bind the at least one additional functional unit to the nanotubule end carboxylate group.

59. The method of claim 58, wherein the at least one additional functional unit is adapted to selectively open or at least partially occlude the pore of an adjacent nanotubule.

60. The method of claim 59, including selecting the at least one additional functional unit from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof.

61. The method of claim 60, including selecting the at least one additional functional unit from the group consisting of biotin, avidin, streptavidin, aliphatic amines, charged dyes, anionically charged ligands, cationically charged ligands, and any combination thereof.

62. The method of claim 59, wherein the at least one additional functional group is a molecule which changes conformation to expose or to at least partially occlude the pore of the adjacent nanotubule in response to an application of an electrical impulse to the membrane.

63. The method of claim 62, wherein the at least one additional functional unit is Direct Blue Dye 71.

64. A method for differentially functionalizing opposed sides of an ordered nanoporous permeable membrane, comprising:
aligning a plurality of hollow nanotubules to form a mat;
coating the mat with a continuous polymer matrix to form a membrane;
etching the membrane to remove a layer of polymer from a surface of the membrane to (a) open the plurality of hollow nanotubules whereby the nanotubules define pores passing through the membrane, and (b) oxidize an end of the nanotubules to form carboxylate groups;
binding at least one first functional unit to the carboxylate groups on a first side of the membrane; and
binding at least one second functional unit to the carboxylate groups on a second, opposed side of the membrane.

65. The method of claim 64, wherein the at least one first functional unit is different from the at least one second functional unit.

66. The method of claim 65, including selecting the first and second at least one additional functional units from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, and any combination thereof.

67. The method of claim 66, including selecting the first and second at least one additional functional units from the group consisting of biotin, avidin, streptavidin, aliphatic amines, charged dyes, anionically charged ligands, cationically charged ligands, and any combination thereof.

68. The method of claim 65, including selecting the first and second at least one additional functional units to reversibly bind to the target molecule.

69. The method of claim 68, further including the step of adding a displacing molecule which displaces the reversibly bound target molecule from the first and second at least one additional functional units.

70. The method of claim 64, wherein the first and second at least one functional units are bound to opposed sides of the membrane by the steps of:
contacting the first side of the membrane with a solution containing the at least one first functional unit; and
contacting the second, opposed side of the membrane with a solution containing the at least one second functional unit.

71. The method of claim 64, wherein the aligned nanotubule mat is coated by dissolving the polymer matrix in a suitable solvent, followed by spin-coating the mat with the polymer-solvent mix.

72. The method of claim 64, including selecting the first and second at least one additional functional units to include at least one available amine group to bind to the nanotubule end carboxylate group.

73. The method of claim 72, wherein the first and second at least one additional functional units are adapted to selectively open or at least partially occlude the pore of an adjacent nanotubule.

74. A differentially functionalized ordered nanoporous permeable membrane, comprising a plurality of aligned hollow nanotubules coated with a continuous polymer matrix to form a membrane, wherein the membrane is etched to remove a layer of polymer from a surface of the membrane to (a) open the plurality of hollow nanotubules whereby the nanotubules define pores passing through the membrane, and (b) oxidize an end of the nanotubules to form carboxylate groups; and
further wherein at least one first functional unit is bound to the carboxylate groups on a first side of the membrane, and at least one second functional unit is bound to the carboxylate groups on a second side of the membrane.

75. The membrane of claim 74, wherein the first and second at least one functional units are bound to opposed sides of the membrane by the steps of:
contacting the first side of the membrane with a solution containing the at least one first functional unit; and
contacting the second, opposed side of the membrane with a solution containing the at least one second functional unit.

76. The membrane of claim 74, wherein each of the plurality of nanotubules includes a hydrophobic lumen.

77. The membrane of claim 74, wherein the nanotubules are selected from the group consisting of multi-walled carbon nanotubes, single-walled carbon nanotubes, self-assembling macromolecular tubules comprising peptides and porphyrins, and any mixture thereof.

78. The membrane of claim 74, wherein the polymer matrix is selected from the group consisting of a thermoset resin, a soluble cast polymer, a castable solidifying sol-gel solution, and any combination thereof.

79. The membrane of claim 78, wherein the polymer matrix is selected from the group consisting of polystyrene, polyimide, polyamide, polymethylmethacrylate, polyolefins, polypropylene, acetylnitrile-butadiene-styrene, acrylic, cellulose acetate, epoxy resin, nylons, polyester thermoset, and any mixture thereof.

80. The membrane of claim 74, wherein the aligned hollow nanotubules are assembled in situ on a substrate.

81. The membrane of claim 80, wherein the aligned nanotubules are removed from the substrate after coating with the polymer matrix.

82. The membrane of claim 74, wherein an oxidative method selected from the group consisting of plasma oxidation, electrochemical oxidation, anodic oxidation, exposure to an oxidizing acid, exposure to ozone, exposure to peroxide, exposure to permanganate, and any combination thereof is used to etch the polymer matrix.

83. The membrane of claim 82, wherein the membrane is selectively etched by electrochemical oxidation.

84. The membrane of claim 74, wherein the at least one first functional unit is different from the at least one second functional unit.

85. The membrane of claim 74, wherein the first and second at least one additional functional units include at least one available amine group to bind to the nanotubule end carboxylate group.

86. The membrane of claim 85, wherein the first and second at least one additional functional units are adapted to selectively open or to at least partially occlude the pore of an adjacent nanotubule.

87. The membrane of claim 86, wherein the first and second at least one additional functional units change conformation to selectively expose or to at least partially occlude the pore of the adjacent nanotubule in response to an application of an electrical impulse to the membrane.

88. The membrane of claim 87, wherein at least one of the at least one first or second additional functional units is Direct Blue Dye 71.

89. The membrane of claim 85, wherein the first and second at least one additional functional units are selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic metal, a catalytic coordination compound, and any combination thereof.

90. The membrane of claim 89, wherein the first and second at least one additional functional units are selected from the group consisting of biotin, avidin, streptavidin, aliphatic amines, charged dyes, anionically charged ligands, cationically charged ligands, and any combination thereof.

* * * * *